(12) United States Patent
Bustamante et al.

(10) Patent No.: US 10,981,137 B2
(45) Date of Patent: *Apr. 20, 2021

(54) ENRICHMENT OF DNA SEQUENCING LIBRARIES FROM SAMPLES CONTAINING SMALL AMOUNTS OF TARGET DNA

(71) Applicant: The Board of Trustees of the Leland Stanford Junior University, Stanford, CA (US)

(72) Inventors: Carlos D. Bustamante, Emerald Hills, CA (US); Meredith L. Carpenter, San Mateo, CA (US); Jason D. Buenrostro, Redwood City, CA (US); William J. Greenleaf, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 10 days.

This patent is subject to a terminal disclaimer.

(21) Appl. No.: 16/743,501

(22) Filed: Jan. 15, 2020

(65) Prior Publication Data

US 2020/0139335 A1    May 7, 2020

Related U.S. Application Data

(63) Continuation of application No. 14/653,748, filed as application No. PCT/US2014/036670 on May 2, 2014, now Pat. No. 10,576,446.

(60) Provisional application No. 61/819,564, filed on May 4, 2013.

(51) Int. Cl.
| | | |
|---|---|---|
| *B01J 19/00* | (2006.01) | |
| *C12Q 1/6806* | (2018.01) | |
| *C12N 15/10* | (2006.01) | |
| *C12Q 1/6809* | (2018.01) | |

(52) U.S. Cl.
CPC ...... *B01J 19/0046* (2013.01); *C12N 15/1006* (2013.01); *C12N 15/1034* (2013.01); *C12Q 1/6806* (2013.01); *C12Q 1/6809* (2013.01); *B01J 2219/00585* (2013.01); *B01J 2219/00596* (2013.01); *B01J 2219/00722* (2013.01)

(58) Field of Classification Search
None
See application file for complete search history.

(56) References Cited

U.S. PATENT DOCUMENTS

| | | |
|---|---|---|
| 5,652,107 A | 7/1997 | Lizardi et al. |
| 5,766,891 A | 6/1998 | Shuman |
| 8,980,553 B2 | 3/2015 | Feehery et al. |
| 2002/0076767 A1 | 6/2002 | Su et al. |
| 2006/0110754 A1 | 5/2006 | Nerenberg et al. |
| 2009/0209751 A1 | 8/2009 | Brevnov et al. |
| 2009/0275087 A1 | 11/2009 | Mikawa |
| 2010/0029498 A1 | 2/2010 | Gnirke et al. |
| 2012/0108440 A1 | 5/2012 | Lau et al. |
| 2012/0178649 A1 | 7/2012 | Watt et al. |
| 2012/0264122 A1 | 10/2012 | Brentano et al. |

FOREIGN PATENT DOCUMENTS

| | | |
|---|---|---|
| WO | WO 2009/099602 A1 | 8/2009 |
| WO | WO 2012/033687 | 3/2012 |
| WO | WO 2012/061600 A1 | 5/2012 |
| WO | WO 2013/164319 | 7/2013 |
| WO | WO 2015/123314 | 8/2015 |

OTHER PUBLICATIONS

Bruzel et al., "DNA Reassociation using Oscillating Phenol Emulsions", Genomics, 2006, 87:286-289.
Carpenter, et al. "Pulling out the 1%: Whole-Genome Capture for the Targeted Enrichment of Ancient DNA Sequencing Libraries", The American Journal of Human Genetics 93, 852-864, 2013.
Gnirke, et al. "Solution Hybrid Selection with Ultra-long Oligonucleotides for Massively Parallel Targeted Sequencing", Nat Biotechnol. Feb. 2009 ; 27(2): 182-189.
Melnikov, et al. "Hybrid selection for sequencing pathogen genomes from clinical samples", Genome Biol 12, R73 (2011).
Josh P. Roberts, "Creative Approaches to Next-Gen Sequencing", Genetic Engineering & Biotechnology News, 2013, 33(5): 23-25.
Michael Knapp, et al. "Next Generation Sequencing of Ancient DNA: Requirements, Strategies and Perspectives", GENES, 2010, 1(2): 227-243.

(Continued)

*Primary Examiner* — Tracy Vivlemore
*Assistant Examiner* — Sahana S Kaup
(74) *Attorney, Agent, or Firm* — James S. Keddie; Bozicevic, Field & Francis LLP

(57) ABSTRACT

Provided herein is a method for capturing DNA molecules in solution. The method may comprise: extracting DNA from a sample that comprises endogenous DNA and environmental DNA to produce extracted DNA; ligating universal adaptors to the extracted DNA; hybridizing the extracted DNA, in solution, with affinity-tagged RNA probes generated by: in vitro transcribing a library of fragmented reference genomic DNA that has been ligated to an RNA promoter adaptor, in the presence of an affinity-tagged ribonucleotide; binding the product with a capture agent that is tethered to a substrate in the presence of RNA oligonucleotides that are complementary to the adaptors, thereby capturing the hybridized DNA molecules on the substrate; washing the substrate to remove any unbound DNA molecules; and releasing the captured DNA molecules. A kit for performing the method is also provided.

23 Claims, 7 Drawing Sheets

Specification includes a Sequence Listing.

(56) References Cited

OTHER PUBLICATIONS

Lesnik et al., "Relative Thermodynamic Stability of DNA, RNA, and DNA:RNA Hybrid Duplexes: Relationship with Base Composition and Structure", Biochemistry, 1995, 34: 10807-10815.
Kidd et al., "Exome capture from saliva produces high quality genomic and metagenomic data", BMC Genomics, 2014, 15:262.
Horn, "Target Enrichment via DNA Hybridization Capture", Ancient DNA, Humana Press, 2012, p. 177-188, published online Dec. 8, 2011.
Sobriera et al. "Chracterization of complex chromosomal rearrangements by targeted capture and next-generation sequencing", Genome Research 21.10, 2011, p. 1720-1727.
Rohland et al., "Cost-effective, high-throughput DNA sequencing libraries for multiplexed target capture", Genome Research 22.5, 2012, p. 939-946.
Wetmur, "DNA Probes: Applications of the Principles of Nucleic Acid Hybridization", Critical reviews in Biochemistry and Molecular Biology, 1991, 26 (3/4): 227-259.

FIG. 2A
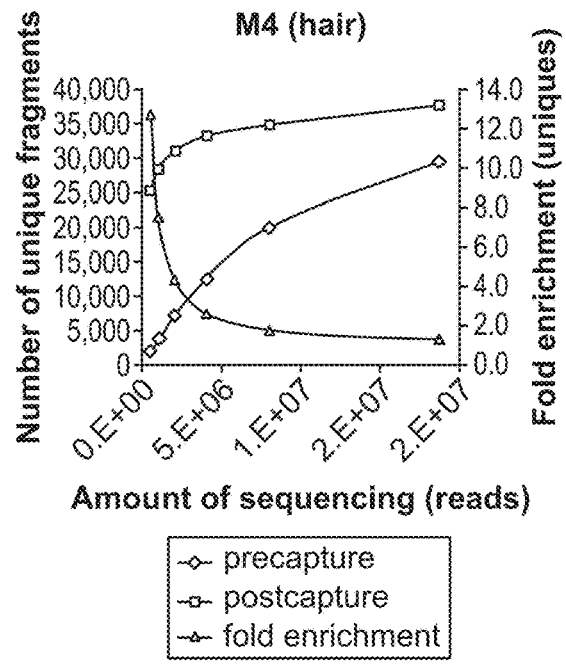
FIG. 2B
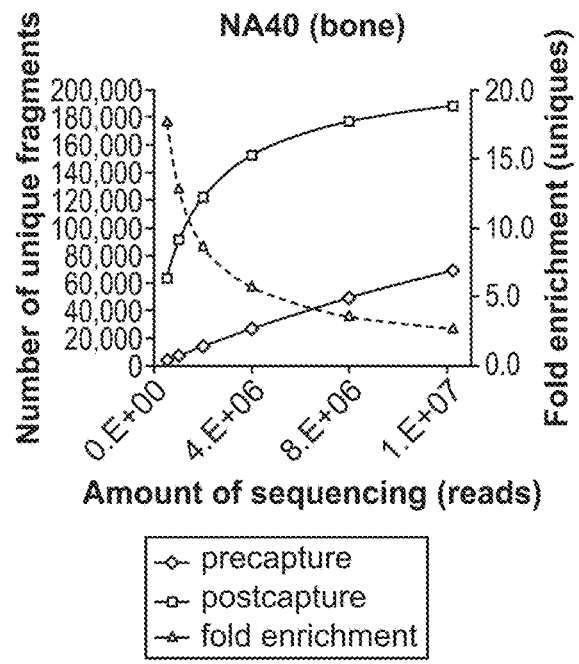
FIG. 2C
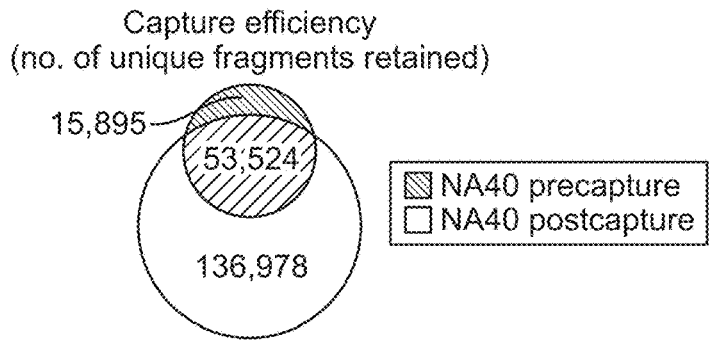
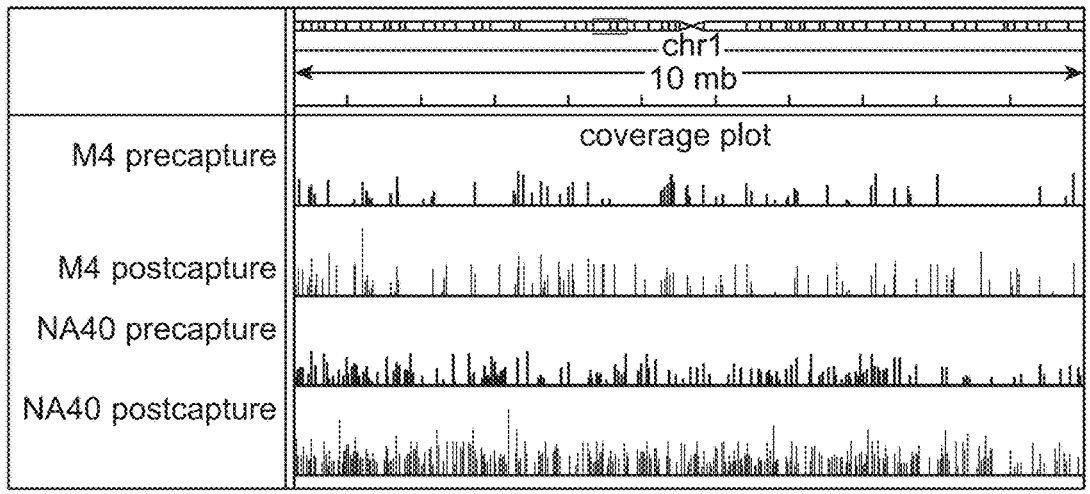
FIG. 2D

| ID | Pre- or Postcapture | Read Pairs (#) | Read Pairs Discarded (Contain Adaptor) (#) | Individual Reads after Merging and Trimming (#) | Mapped Human Reads (%) | Fold Enrichment in # Mapped[a] | Unique Reads (%) |
|---|---|---|---|---|---|---|---|
| Bulgaria 1500-500 BC Tooth | | | | | | | |
| V2 | pre | 1,390,960 | 98,697 | 1,331,130 | 0.30% | | 0.30% |
| | post | 1,390,960 | 30,681 | 1,446,302 | 20.20% | 70 | 2.70% |
| P192-1 | pre | 819,844 | 118,493 | 705,234 | 4.30% | | 3.90% |
| | post | 819,844 | 14,993 | 829,256 | 23.20% | 6 | 7.80% |
| T2G2 | pre | 1,596,526 | 20,644 | 1,633,734 | 0.05% | | 0.05% |
| | post | 1,596,526 | 16,168 | 1,870,076 | 7.40% | 159 | 0.30% |
| K8 | pre | 1,817,223 | 76,872 | 1,980,966 | 1.00% | | 0.80% |
| | post | 1,817,223 | 15,322 | 2,537,422 | 36.00% | 48 | 3.40% |
| Denmark - 1350 BC Hair | | | | | | | |
| M4 | pre | 1,000,000 | 210,491 | 828,494 | 0.50% | | 0.50% |
| | post | 1,000,000 | 26,695 | 1,269,181 | 36.60% | 114 | 2.20% |
| Peru - 900-1500 AD Bone | | | | | | | |
| NA39 | pre | 1,000,000 | 50,534 | 1,192,685 | 1.100% | | 1.00% |
| | post | 1,000,000 | 6,472 | 1,419,774 | 59.500% | 62 | 2.10% |
| NA40 | pre | 1,000,000 | 89,763 | 1,010,267 | 0.720% | | 0.70% |
| | post | 1,000,000 | 24,214 | 1,191,241 | 26.500% | 44 | 7.70% |
| NA41 | pre | 1,000,000 | 76,485 | 1,358,860 | 0.300% | | 0.30% |
| | post | 1,000,000 | 12,319 | 1,628,753 | 23.200% | 92 | 1.30% |
| NA42 | pre | 1,000,000 | 74,460 | 1,117,389 | 6.200% | | 4.90% |
| | post | 1,000,000 | 14,847 | 1,341,546 | 41.000% | 8 | 7.90% |
| NA43 | pre | 1,000,000 | 116,780 | 966,013 | 0.180% | | 0.20% |
| | post | 1,000,000 | 81,544 | 1,036,263 | 7.400% | 45 | 0.60% |
| NA47 | pre | 1,000,000 | 92,800 | 973,662 | 0.130% | | 0.10% |
| | post | 1,000,000 | 32,741 | 1,107,880 | 9.100% | 77 | 0.80% |
| NA50 | pre | 1,000,000 | 126,605 | 1,001,135 | 0.035% | | 0.03% |
| | post | 1,000,000 | 37,653 | 1,292,570 | 1.700% | 61 | 0.30% |

The first four samples were adjusted to have identical numbers of pre- and postcapture reads, based on samples were adjusted to 1 million reads each for ease of comparison with the first four samples. Prior to from both merged and unmerged reads (note that the number of reads listed after merging and trimming filtered for mapping qualities ≥ 30. Overlap with repeats was determined by intersection with the
[a] Does not vary with amount of sequencing
[b] Varies with library complexity and amount of sequencing

FIG. 4

| Fold Enrichment in # Uniques[b] | Duplicate Reads (of Mapped) (%) | Precapture Reads Present in Postcapture (%) | Positions Covered (#) | Reads in Repeats (%) | Fold mtDNA Coverage | SNPs Overlapping with 1000G (#) |
|---|---|---|---|---|---|---|
|  | 9% |  | 38,908 | 34% | 0.01 | 5,281 |
| 10 | 87% | 46% | 4,077,324 | 45% | 0.40 | 40,583 |
|  | 9% |  | 2,248,978 | 35% | 0.30 | 30,081 |
| 2 | 66% | 52% | 5,000,399 | 45% | 2.00 | 67,221 |
|  | 14% |  | 45,111 | 33% | 0.30 | 597 |
| 8 | 96% | 15% | 303,848 | 30% | 16.1 | 4,068 |
|  | 14% |  | 1,506,968 | 35% | 0.06 | 19,960 |
| 5 | 90% | 90% | 7,093,382 | 37% | 0.30 | 94,394 |
|  | 7% |  | 364,855 | 35% | 0.06 | 5,115 |
| 8 | 94% | 70% | 3,152,432 | 37% | 0.60 | 40,340 |
|  | 14% |  | 1,066,246 | 34% | 5.30 | 14,751 |
| 3 | 96% | 56% | 4,301,252 | 37% | 19.90 | 40,048 |
|  | 2% |  | 642,917 | 36% | 0.05 | 9,119 |
| 13 | 70% | 42% | 17,253,987 | 38% | 2.70 | 129,872 |
|  | 10% |  | 334,441 | 33% | 0.01 | 4,621 |
| 6 | 94% | 75% | 1,966,403 | 36% | 0.60 | 26,118 |
|  | 20% |  | 5,197,492 | 36% | 3.50 | 73,266 |
| 2 | 80% | 57% | 16,609,757 | 37% | 10.90 | 147,243 |
|  | 11% |  | 113,616 | 38% | 0.01 | 1,553 |
| 4 | 91% | 68% | 579,192 | 40% | 0.40 | 6,337 |
|  | 4% |  | 93,784 | 38% | 0.01 | 1,279 |
| 7 | 90% | 58% | 833,067 | 42% | 0.50 | 9,393 |
|  | 3% |  | 15,135 | 40% | 0.00 | 217 |
| 10 | 78% | 24% | 377,875 | 43% | 0.50 | 3,062 | the number of reads obtained from MiSeq sequencing of the postcapture libraries. The last eight mapping, overlapping paired-end reads were computationally merged, and adapters were trimmed includes both forward and reverse reads for pairs that were not merged). Mapped reads were RepeatMasker annotation of human genome repeats. 1000G: 1000 Genomes reference panel.

FIG. 4 (Cont.)

ENRICHMENT OF DNA SEQUENCING LIBRARIES FROM SAMPLES CONTAINING SMALL AMOUNTS OF TARGET DNA

CROSS-REFERENCING

This application is a continuation of U.S. application Ser. No. 14/653,748, filed on Jun. 18, 2015, which is a § 371 national phase of International Application No. PCT/US2014/036670, filed on May 2, 2014, which claims the benefit of U.S. Provisional application Ser. No. 61/819,564, filed on May 4, 2013, which applications are incorporated by reference herein in their entireties.

GOVERNMENT SUPPORT

This invention was made with Government support under grant nos. HG005715 and HG003229 awarded by the National Institutes of Health (NIH). The Government has certain rights in the invention.

BACKGROUND

The very low levels of endogenous DNA remaining in most ancient specimens has precluded the shotgun sequencing of many interesting samples due to cost. For example, ancient DNA (aDNA) libraries derived from bones and teeth often contain <1% endogenous DNA, meaning that the majority of sequencing capacity is taken up by environmental DNA. Thus much of the cost associated with sequencing low endogenous DNA sample provides no human genome data. As a result, many ancient DNA samples are considered unsuitable for sequencing because the data yield is low compared to the resources required. Thus there is a need in the art to increase endogenous DNA yield in low endogenous DNA samples and specifically to increase the percent of endogenous DNA being sequenced when sequencing low endogenous DNA samples.

Recent developments in DNA extraction have provided lower cost next-generation sequencing techniques to the point that the field of paleogenetics has transitioned from focusing on PCR-amplified mitochondrial DNA and Y-chromosomal markers to shotgun sequencing of the whole genome. However, shotgun sequencing can yield less than desirable results when sequencing low endogenous DNA samples due to the low percentage of endogenous DNA in the overall sample material.

Instead, the use of autosomal DNA sequences may be superior for population genetic analysis because it provides information from both lineages (i.e., maternal and paternal). Thus there exists a specific need in the art to provide an autosomal DNA sequencing technique for ancient DNA analysis in order to derive improved resolution for population genetic analysis. For example, whole genome sequencing of single ancient genomes, including Neanderthals, Denisovan, a Paleo-Eskimo, the Tyrolean Iceman, and an Australian Aborigine, have transformed our understanding of human migrations and revealed previously unknown admixture among ancient populations. However, most of these specimens were exceptional in their levels of preservation: the Neanderthal and Denisovan bones, found in caves, contained ~1-5% and 70% endogenous DNA, respectively, while the Paleo-Eskimo and Aborigine genomes were obtained from hair specimens, which generally contain lower levels of contamination but are not available in most archaeological contexts.

In contrast, sequencing libraries derived from bones and teeth from temperate environments typically contain <1% endogenous DNA. While samples with 1-2% endogenous DNA can still, with sufficient sequencing, yield enough information for population genetic analyses, the required amount of sequencing of specimens with less DNA is costly and thus untenable for many researchers. Ancient DNA researchers have begun to address this issue by using targeted capture to enrich for only the mtDNA or for a single chromosome. However, due to the highly fragmented nature of ancient DNA, an ideal enrichment technique would extract as much of the endogenous genome as possible so as not to discard any potentially informative sequences. Similar problems exist in forensics.

SUMMARY

Provided herein is a method for capturing DNA molecules in solution. In certain embodiments, the method comprises: a) extracting DNA from a sample that comprises endogenous DNA and environmental DNA to produce extracted DNA, wherein the extracted DNA comprises more environmental DNA than endogenous DNA; b) ligating a universal adaptor to the extracted DNA; c) hybridizing the extracted DNA, in solution, with affinity-tagged RNA probes generated by: in vitro transcribing, in the presence of a affinity-tagged ribonucleotide, a library comprising fragmented reference genomic DNA that has been ligated to an RNA promoter adaptor; d) binding the product of step c) with a capture agent for the affinity tag that is tethered to a substrate in the presence of RNA oligonucleotides that are complementary to the adaptors, thereby capturing the hybridized DNA molecules on the substrate; e) washing the substrate to remove any unbound DNA molecules; and f) releasing the captured DNA molecules. A kit for performing the method is also provided.

These and other features of the present teachings are set forth herein.

BRIEF DESCRIPTION OF THE FIGURES

The skilled artisan will understand that the drawings, described below, are for illustration purposes only. The drawings are not intended to limit the scope of the present teachings in any way.

FIG. 2A-2F shows the results of increased Sequencing of Samples M4 and NA40. (FIG. 2A) Yield of unique fragments for M4 (Bronze Age hair) precapture (blue) and postcapture (red) libraries with increasing amounts of sequencing. The fold enrichment in number of unique reads with increasing amounts of sequencing is plotted in green, with values on the secondary y axis. (FIG. 2B) Yield of unique fragments for NA40 (Peruvian bone) precapture (blue) and postcapture (red) libraries with increasing amounts of sequencing. The fold enrichment in number of unique reads with increasing amounts of sequencing is plotted in green, with values on the secondary y axis. (FIG. 2C) Venn diagram showing the overlap between the NA40 pre- and postcapture libraries based on sequencing of 12.3 million reads. (FIG. 2D) Coverage plot of the M4 and NA40 libraries based on sequencing of 18.6 million and 12.3 million reads, respectively. Shown is a random 10-megabase segment of chromosome 1. Coverage was calculated in 1 kb windows across the region. (FIG. 2E) Insert size distribution for NA40 pre- and postcapture libraries. (FIG. 2F) Percent GC content of reads for NA40 pre- and postcapture libraries.

(FIG. 3C) M4 (Bronze Age hair) precapture and (FIG. 3D) postcapture; and (FIG. 3E) NA40 (Peruvian bone) precapture and (FIG. 3F) postcapture. Population key: ASW, Americans of African ancestry in SW USA; AYM, Aymara from the Peruvian Andes; CEU, Utah residents (CEPH) with Northern and Western European ancestry; CHB, Han Chinese in Beijing, China; CHS, Southern Han Chinese; CLM, Colombians from Medellin, Columbia; FIN, Finnish in Finland; GBR, British in England and Scotland; IBS, Iberian population in Spain; JPT, Japanese in Tokyo, Japan; KAR, Karitiana from the Brazilian Amazon; LWK, Luhya in Webuye, Kenya; MAY, Mayan from Mexico; MXL, Mexican ancestry from Los Angeles, USA; PUR, Puerto Ricans from Puerto Rico; TSI, Toscani in Italy; YRI, Yoruba in Ibadan, Nigeria.

FIG. 4 shows data obtained from various sequencing experiments.

DEFINITIONS

Figure 1:
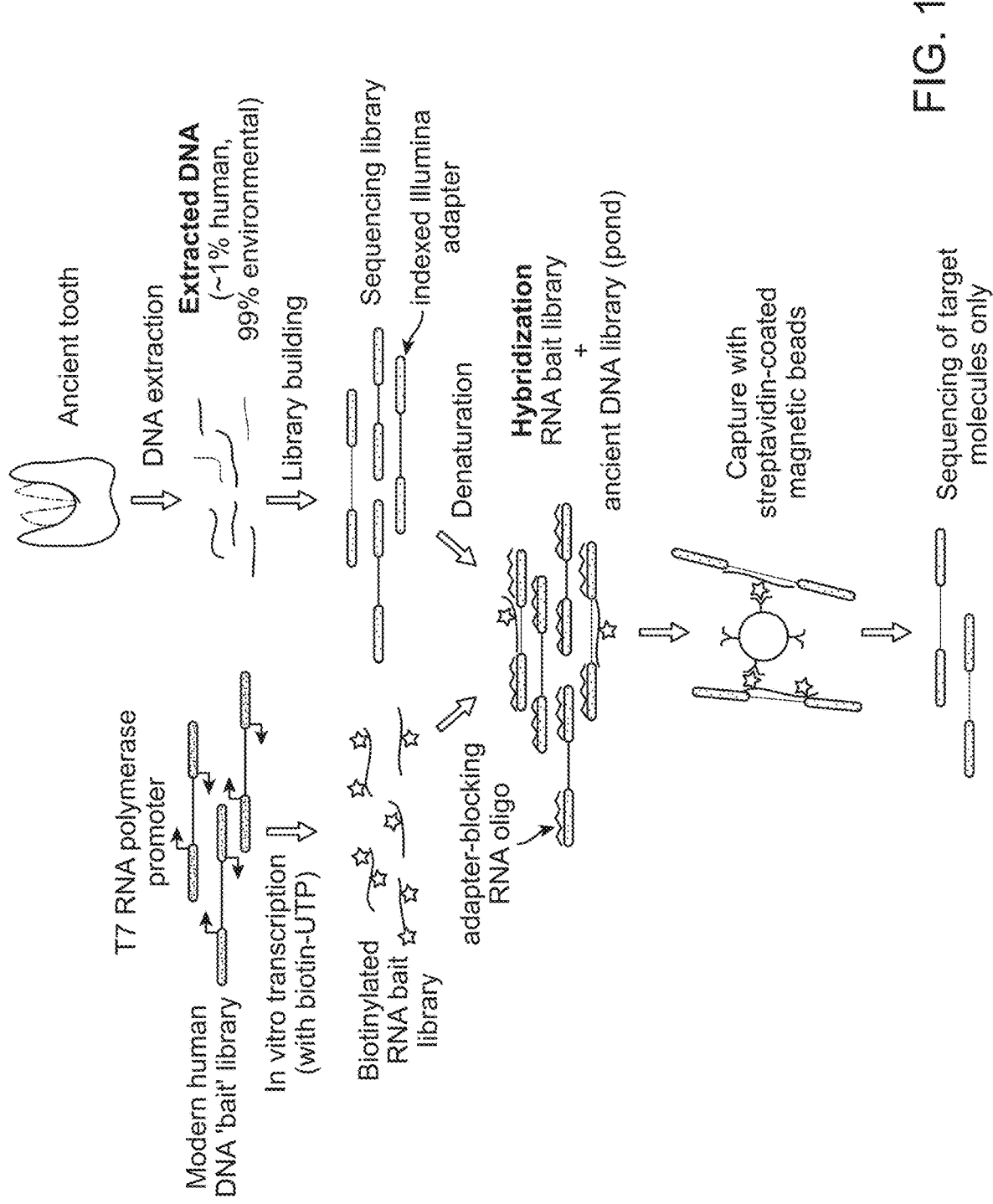
FIG. 1 schematically illustrates a Whole-Genome In-Solution Capture Process. To generate the RNA "bait" library, a human genomic library is created via adapters containing T7 RNA polymerase promoters (green boxes). This library is subjected to in vitro transcription via T7 RNA polymerase and biotin-16-UTP (stars), creating a biotinylated bait library. Meanwhile, the ancient DNA library (aDNA "pond") is prepared via standard indexed Illumina adapters (purple boxes). These aDNA libraries often contain <1% endogenous DNA, with the remainder being environmental in origin. During hybridization, the bait and pond are combined in the presence of adaptor-blocking RNA oligos (blue zigzags), which are complimentary to the indexed Illumina adapters and thus prevent nonspecific hybridization between adapters in the aDNA library. After hybridization, the biotinylated bait and bound aDNA is pulled down with streptavidin-coated magnetic beads, and any unbound DNA is washed away. Finally, the DNA is eluted and amplified for sequencing.

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

The term "sample" as used herein relates to a material or mixture of materials, typically, although not necessarily, in liquid form, containing one or more analytes of interest.

The term "nucleic acid sample," as used herein denotes a sample containing nucleic acids. Nucleic acid samples used herein may be complex in that they contain multiple different molecules that contain sequences. Genomic DNA from a mammal (e.g., mouse or human) are types of complex samples. Complex samples may have more then $10^4$, $10^5$, $10^6$ or $10^7$ different nucleic acid molecules. A DNA target may originate from any source such as genomic DNA, or an artificial DNA construct. Any sample containing nucleic acid, e.g., genomic DNA made from tissue culture cells or a sample of tissue, may be employed herein. A nucleic acid sample can be made from any suitable source, including a sample of tooth, bone, hair or bone, etc.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The term "nucleic acid" and "polynucleotide" are used interchangeably herein to describe a polymer of any length, e.g., greater than about 2 bases, greater than about 10 bases, greater than about 100 bases, greater than about 500 bases, greater than about 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine and thymine (G, C, A and T, respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylene carbonyl bonds. A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid," or "UNA," is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA. Also included in this definition are ZNAs, i.e., zip nucleic acids.

The term "oligonucleotide" as used herein denotes a single-stranded multimer of nucleotide of from about 2 to 200 nucleotides, up to 500 nucleotides in length. Oligonucleotides may be synthetic or may be made enzymatically, and, in some embodiments, are 30 to 150 nucleotides in length. Oligonucleotides may contain ribonucleotide monomers (i.e., may be oligoribonucleotides) and/or deoxyribonucleotide monomers. An oligonucleotide may be 10 to 20, 21 to 30, 31 to 40, 41 to 50, 51 to 60, 61 to 70, 71 to 80, 80 to 100, 100 to 150 or 150 to 200 nucleotides in length, for example.

The term "hybridization" refers to the process by which a strand of nucleic acid joins with a complementary strand through base pairing as known in the art. A nucleic acid is considered to be "selectively hybridizable" to a reference nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions includes hybridization at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C.

The term "duplex," or "duplexed," as used herein, describes two complementary polynucleotides that are base-paired, i.e., hybridized together.

The term "amplifying" as used herein refers to generating one or more copies of a target nucleic acid, using the target nucleic acid as a template.

The terms "determining," "measuring," "evaluating," "assessing," "assaying," and "analyzing" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

As used herein, the term "$T_m$" refers to the melting temperature of an oligonucleotide duplex at which half of the duplexes remain hybridized and half of the duplexes dissociate into single strands. The $T_m$ of an oligonucleotide duplex may be experimentally determined or predicted using the following formula $T_m=81.5+16.6(\log_{10}[Na^+])+0.41$ (fraction G+C)−(60/N), where N is the chain length and [$Na^+$] is less than 1 M. See Sambrook and Russell (2001; Molecular Cloning: A Laboratory Manual, $3^{rd}$ ed., Cold Spring Harbor Press, Cold Spring Harbor N.Y., Ch. 10). Other formulas for predicting $T_m$ of oligonucleotide duplexes exist and one formula may be more or less appropriate for a given condition or set of conditions.

The term "partitioning," with respect to a genome, refers to the separation of one part of the genome from the remainder of the genome to produce a product that is isolated from the remainder of the genome. The term "partitioning" encompasses enriching.

The term "genomic region," as used herein, refers to a region of a genome, e.g., an animal or plant genome such as the genome of a human, monkey, rat, fish or insect or plant. In certain cases, an oligonucleotide used in the method described herein may be designed using a reference genomic region, i.e., a genomic region of known nucleotide sequence, e.g., a chromosomal region whose sequence is deposited at NCBI's Genbank database or other databases, for example.

The term "genomic sequence," as used herein, refers to a sequence that occurs in a genome. Because RNAs are transcribed from a genome, this term encompasses sequence that exist in the nuclear genome of an organism, as well as sequences that are present in a cDNA copy of an RNA (e.g., an mRNA) transcribed from such a genome.

The term "genomic fragment," as used herein, refers to a region of a genome, e.g., an animal or plant genome such as the genome of a human, monkey, rat, fish or insect or plant. A genomic fragment may be an entire chromosome, or a fragment of a chromosome. A genomic fragment may be adaptor ligated (in which case it has an adaptor ligated to one or both ends of the fragment, or to at least the 5' end of a molecule), or may not be adaptor ligated.

In certain cases, an oligonucleotide used in the method described herein may be designed using a reference genomic region, i.e., a genomic region of known nucleotide sequence, e.g., a chromosomal region whose sequence is deposited at NCBI's Genbank database or other databases, for example. Such an oligonucleotide may be employed in an assay that uses a sample containing a test genome, where the test genome contains a binding site for the oligonucleotide.

As used herein, the term "biotin moiety" refers to an affinity agent that includes biotin or a biotin analogue such as desthiobiotin, oxybiotin, 2-iminobiotin, diaminobiotin, biotin sulfoxide, biocytin, etc. Biotin moieties bind to streptavidin with an affinity of at least $10^{-8}$ M. A biotin affinity agent may also include a linker, e.g., -LC-biotin, -LC-LC-Biotin, -SLC-Biotin or -PEG$_n$-Biotin where n is 3-12.

The term "ligating," as used herein, refers to the enzymatically catalyzed joining of the terminal nucleotide at the 5' end of a first DNA molecule to the terminal nucleotide at the 3' end of a second DNA molecule. A transposase can catalyze a ligation.

A "plurality" contains at least 2 members. In certain cases, a plurality may have at least 10, at least 100, at least 100, at least 10,000, at least 100,000, at least $10^6$, at least $10^7$, at least $10^8$ or at least $10^9$ or more members.

If two nucleic acids are "complementary," each base of one of the nucleic acids base pairs with corresponding nucleotides in the other nucleic acid. Two nucleic acids do not need to be perfectly complementary in order to hybridize to one another.

The term "separating," as used herein, refers to physical separation of two elements (e.g., by size or affinity, etc.) as well as degradation of one element, leaving the other intact.

In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, the "first" and "second" strands, the "coding" and "noncoding" strands, the "Watson" and "Crick" strands or the "sense" and "antisense" strands. The assignment of a strand as being a top or bottom strand is arbitrary and does not imply any particular orientation, function or structure. Until they become covalently linked, the first and second strands are distinct molecules. For ease of description, the "top" and "bottom" strands of a double-stranded nucleic acid in which the top and bottom strands have been covalently linked will still be described as the "top" and "bottom" strands. In other words, for the purposes of this disclosure, the top and bottom strands of a double-stranded DNA do not need to be separated molecules. The nucleotide sequences of the first strand of several exemplary mammalian chromosomal regions (e.g., BACs, assemblies, chromosomes, etc.) is known, and may be found in NCBI's Genbank database, for example.

The term "top strand," as used herein, refers to either strand of a nucleic acid but not both strands of a nucleic acid. When an oligonucleotide or a primer binds or anneals "only to a top strand," it binds to only one strand but not the other. The term "bottom strand," as used herein, refers to the strand that is complementary to the "top strand." When an oligonucleotide binds or anneals "only to one strand," it binds to only one strand, e.g., the first or second strand, but not the other strand. If an oligonucleotide binds or anneals to both strands of a double-stranded DNA, the oligonucleotide may have two regions, a first region that hybridizes with the top strand of the double-stranded DNA, and a second region that hybridizes with the bottom strand of the double-stranded DNA.

The term "double-stranded DNA molecule" refers to both double-stranded DNA molecules in which the top and bottom strands are not covalently linked, as well as double-stranded DNA molecules in which the top and bottom stands are covalently linked. The top and bottom strands of a double-stranded DNA are base paired with one other by Watson-Crick interactions.

The term "denaturing," as used herein, refers to the separation of at least a portion of the base pairs of a nucleic acid duplex by placing the duplex in suitable denaturing conditions. Denaturing conditions are well known in the art. In one embodiment, in order to denature a nucleic acid duplex, the duplex may be exposed to a temperature that is above the $T_m$ of the duplex, thereby releasing one strand of the duplex from the other. In certain embodiments, a nucleic acid may be denatured by exposing it to a temperature of at least 90° C. for a suitable amount of time (e.g., at least 30 seconds, up to 30 mins). In certain embodiments, fully denaturing conditions may be used to completely separate the base pairs of the duplex. In other embodiments, partially denaturing conditions (e.g., with a lower temperature than fully denaturing conditions) may be used to separate the base pairs of certain parts of the duplex (e.g., regions enriched for A-T base pairs may separate while regions enriched for G-C base pairs may remain paired). Nucleic acid may also be denatured chemically (e.g., using urea or NaOH).

The term "genotyping," as used herein, refers to any type of analysis of a nucleic acid sequence, and includes sequencing, polymorphism (SNP) analysis, and analysis to identify rearrangements.

The term "sequencing," as used herein, refers to a method by which the identity of at least 10 consecutive nucleotides (e.g., the identity of at least 20, at least 50, at least 100 or at least 200 or more consecutive nucleotides) of a polynucleotide are obtained.

The term "next-generation sequencing" refers to the so-called parallelized sequencing-by-synthesis or sequencing-by-ligation platforms currently employed by Illumina, Life Technologies, and Roche, etc. Next-generation sequencing methods may also include nanopore sequencing methods or electronic-detection based methods such as Ion Torrent technology commercialized by Life Technologies.

The term "endogenous DNA" refers to DNA that is present in a sample (e.g., a sample of tooth, bone, hair or bone) that is naturally associated with the sample when the sample was part of a living being.

The term "environmental DNA" refers to DNA that is present in a sample (e.g., a sample of tooth, bone, hair or bone) that was not naturally associated with the sample when the sample was part of a living being. Environmental DNA can come from a variety of sources, including, but not limited to microbes that have contaminated the sample. In some cases, the contaminating DNA may be genomic DNA from microbes that have grown on or in the sample over time. In other cases, the sample may have been placed in an environment, e.g., soil or feces, that contains a significant amount of contaminating DNA.

The term "reference genomic DNA" refers to genomic DNA from a species of interest. The species of interest may be eukaryotic or prokaryotic, including animal (e.g., mammalian), plant, and bacterial, species. Reference genomic DNA is selected so that it hybridizes to the endogenous DNA and not the environmental DNA at high stringency.

The term "adaptor" refers to a nucleic acid that is ligatable to both strands of a double-stranded DNA molecule. In one embodiment, an adaptor may be a hairpin adaptor (i.e., one molecule that base pairs with itself to form a structure that has a double-stranded stem and a loop, where the 3' and 5' ends of the molecule ligate to the 5' and 3' ends of the double-stranded DNA molecule, respectively). In another embodiment, an adaptor may be a Y-adaptor. In another embodiment, an adaptor may itself be composed of two distinct oligonucleotide molecules that are base paired with one another. As would be apparent, a ligatable end of an adaptor may be designed to be compatible with overhangs made by cleavage by a restriction enzyme, or it may have blunt ends or a 5' T overhang. The term "adaptor" refers to double-stranded as well as single-stranded molecules. An adaptor can be DNA or RNA, or a mixture of the two. An adaptor containing RNA may be cleavable by RNase treatment or by alkaline hydrolysis. An adaptor may be 15 to 100 bases, e.g., 50 to 70 bases, although adaptors outside of this range are envisioned.

The term "adaptor-ligated," as used herein, refers to a nucleic acid that has been ligated to an adaptor. The adaptor can be ligated to a 5' end and/or a 3' end of a nucleic acid molecule.

The term "universal adaptor" refers to an adaptor that is ligated to both ends of the nucleic acid molecules under study. In certain embodiments, the universal adaptor may be a Y-adaptor. Amplification of nucleic acid molecules that have been ligated to Y-adaptors at both ends results in an asymmetrically tagged nucleic acid, i.e., a nucleic acid that has a 5' end containing one tag sequence and a 3' end that has another tag sequence.

The term "Y-adaptor" refers to an adaptor that contains: a double-stranded region and a single-stranded region in which the oligonucleotides are not complementary. The end of the double-stranded region ligates to target molecules such as double-stranded fragments of genomic DNA. Each strand of an adaptor-tagged double-stranded DNA that has been ligated to a Y adaptor is asymmetrically tagged in that it has the sequence of one strand of the Y-adaptor at one end and the other strand of the Y-adaptor at the other end.

The term "RNA promoter adaptor" is an adaptor that contains a promoter for a bacteriophage RNA polymerase, e.g., the RNA polymerase from bacteriophage T3, T7, SP6 or the like.

The terms "affinity tag" and "capture agent" refer to a moieties that are capable of: a) specifically binding to one other non-covalently or b) selectively reacting one another to form a covalent bond. Examples of pairs of suitable affinity tags and capture agents that specifically bind to one another non-covalently are numerous and include, but are not limited to: streptavidin/avidin, digoxigenin/anti-digoxigenin antibody, fluorescein/anti-fluorescein antibody, although many others are known. Examples of chemoselective reactive groups that selectively react with one another to form a covalent bond are numerous and include: amines and active esters such as an NHS esters, thiols and maleimide or iodoacetamide), as well as groups that can react with one another via Click chemistry, e.g., azide and alkyne groups. Ribonucleotides that contain affinity tags that can be used herein are available commercially from many sources.

The term "biotinylated ribonucleotide" refers to a ribonucleotide triphosphate (e.g., ATP, GTP, CTP and UTP) that is linked to a biotin moiety. Bio-16-UTP (Biotin-16-uridine-5'-triphosphate) is an example of a biotinylated ribonucleotide that can replace UTP for in vitro transcription reaction catalyzed by T3, T7 or SP6 RNA polymerases.

Other definitions of terms may appear throughout the specification.

DESCRIPTION OF EXEMPLARY EMBODIMENTS

An example of the method is shown in FIG. 1. In certain embodiments, the method may start by extracting DNA from a sample that comprises: both endogenous DNA and environmental DNA, to produce extracted DNA. In these embodiments, the extracted DNA may comprise more (at least 2 times, at least 5 times, at least 10 times, at least 50 times, or at least 100 times, at least 500 times or at least 1,000 times more) environmental DNA than endogenous DNA. Methods for extracting DNA from various samples, e.g., clinical, forensic, archaeological and environmental samples, are well known in the art. The DNA in these samples may be highly fragmented, e.g., to an average size in the range of 10 bp to 5 kb, e.g., 20 bp to 200 bp (see, e.g., Sawyer et al, PLoS ONE 7: e34131). In particular embodiments, the sample may be a sample of a hard tissue such as bone, hair, nail or tooth, from an ancient source (e.g., a source that died at least 10 years ago, at least 100 years ago or a source that died at least 1,000 years ago, such as a mummy, hard tissue found in a burial site or the like). Methods for extracting DNA from such tissues are known (see, e.g., Higgins et al (Sci Justice 2013 53:433-41), Knapp et al (Ann. Anat. 2012 194: 3-6), Amory et al (Forensic Sci. Int. 2007 166: 218-29) and Benoit et al (Med. Sci. Law. 2013 53:100-6) and Rohland (Methods Mol. Biol. 2012 840: 21-8). Methods for extracting DNA from forensic samples, e.g., samples from a crime scene, are well known.

After extracting the DNA from the sample, the DNA is ligated to a universal adaptor, i.e., an adaptor that ligates to both ends of the fragments of DNA contained in the extracted DNA sample. In certain cases, the universal adaptor may be a Y-adaptor, an example of which is described below. In particular cases, the ligating may be done by polishing the ends of the extracted DNA using a polymerase, and then ligating the adaptor via a blunt-end ligation. In other embodiments, the ends may be polished using Taq polymerase, which adds an additional 3' A (thereby producing a 3' A overhang), and the ligating may be done using an adaptor that has a 5' T overhang. As would be apparent, the adaptor may be "indexed" in that it contains a molecular barcode that identifies the sample to which it was ligated (which allows samples to be pooled before sequencing). Alternatively or in addition, the adaptor may contain a random barcode or the like. Such an adaptor can be ligated to the fragments and substantially every fragment corresponding to a particular region are tagged with a different sequence. This allows for identification of PCR duplicates and allows molecules to be counted.

After adaptor ligation, the sample may be optionally amplified, by PCR, for example. In these embodiments, the adaptor-ligated nucleic acids in the sample may be amplified using one or more primers that hybridize to the added adaptors (or their complements). In embodiments in which Y-adaptors are added, the adaptor-ligated nucleic acids may be amplified by PCR using two primers: a first primer that hybridizes to the single-stranded region of the top strand of the adaptor, and a second primer that hybridizes to the complement of the single-stranded region of the bottom strand of the adaptor. After the adaptors have been added to the nucleic acid in the sample and the adaptor-ligated nucleic acid has been optionally amplified, the adaptor-ligated nucleic acid may be hybridized in solution under high stringency with affinity-tagged RNA probes that have been generated by in vitro transcribing a library of a reference genomic sample that has been ligated to an RNA promoter adaptor (e.g., a T7 promoter), in the presence of an affinity-tagged ribonucleotide. The reference sample may be from a species that is similar or identical to the source of the endogenous DNA, i.e., sufficiently similar that their DNAs will hybridize at high stringency (e.g., at a temperature of at least 42° C., at least 50° C. or at least 60° C. for at least 24 hr). In certain embodiments, the hybridization may be done by phenol emulsion reassociation (PERT) (Miller at al, Nucleic Acids Res. 1995 23: 2339-2340) or oscillating phenol emulsion reassociation (osPERT) (Bruzel et al Genomics. 2006 87:286-9) in order to reassociate the sequences rapidly.

The reference sample may be, for example, (e.g., human) genomic DNA that has been fragmented to a desired size, e.g., an average size in the range of 100 bp to 10 kb, e.g., 100 bp to 500 bp, although sizes outside of these ranges are envisioned. Such fragments may be made by fragmenting a genome using physical methods (e.g., sonication, nebulization, or shearing), chemically, enzymatically (e.g., using a rare-cutting restriction enzyme) or using a transposable element. After fragmentation, the fragments may be ligated to an RNA polymerase promoter using conventional methods. The RNA polymerase promoter can also be added to the fragments during cleavage if a transposon is used. The fragments to which the RNA promoter has been ligated can then be transcribed in vitro into affinity-tagged RNA probes. In certain cases the reference sample may be processed to select for or remove particular sequences. For example, the reference sample may be processed to remove repetitive sequences, e.g., microsatellite sequences, LINEs and/or SINEs, etc., before use.

After hybridization in solution, the hybridized DNA molecules are captured on a substrate, e.g., a solid support or beads. In these embodiments, the hybridized product is bound to a substrate that comprises a capture agent for the affinity tag, and the affinity tag binds to the capture agent. This step may be done in the presence of one or more RNA oligonucleotides that are complementary to or have the same sequence as one or more strands of the universal adaptor. In certain cases, these RNA oligonucleotides may themselves be made using in vitro transcription, e.g., by annealing two oligonucleotides together to produce a duplex that comprises a double-stranded RNA promoter upstream from a transcribed region, where the transcribed region can be transcribed to produce an RNA oligonucleotide. In these embodiments, the RNA oligonucleotides may be complementary to or have the same sequence as at least 50% (e.g., at least 60%, at least 70% or more) of the contiguous sequence of the universal adaptor.

After capture, the substrate is washed to remove any unbound DNA molecules, and the captured DNA molecules can be released. In some embodiments, the captured DNA molecules are released by treating the support with NaOH, which cleaves the in vitro transcribed RNA molecules, thereby releasing the DNA molecules. This step could be performed by treatment with RNaseH, RNaseA, or by heating the substrate to a temperature that is sufficient to denature the duplexes attached thereto.

After the captured DNA molecules have been released, they may be optionally amplified (e.g., using primers that hybridize to the added adaptor sequences or their complements) and sequenced. In certain embodiments, the released DNA may be amplified using primers that are compatible with use in, e.g., Illumina's reversible terminator method, Roche's pyrosequencing method (454), Life Technologies' sequencing by ligation (the SOLiD platform) or Life Technologies' Ion Torrent platform. Examples of such methods are described in the following references: Margulies et al (Nature 2005 437: 376-80); Ronaghi et al (Analytical Biochemistry 1996 242: 84-9); Shendure et al (Science 2005 309: 1728-32); Imelfort et al (Brief Bioinform. 2009 10:609-18); Fox et al (Methods Mol Biol. 2009; 553:79-108); Appleby et al (Methods Mol Biol. 2009; 513:19-39) and Morozova et al (Genomics. 2008 92:255-64), which are incorporated by reference for the general descriptions of the methods and the particular steps of the methods, including all starting products, reagents, and final products for each of the steps.

In another embodiment, the released DNA may be sequenced using nanopore sequencing (e.g., as described in Soni et al. Clin Chem 2007 53: 1996-2001, or as described by Oxford Nanopore Technologies). Nanopore sequencing is a single-molecule sequencing technology whereby a single molecule of DNA is sequenced directly as it passes through a nanopore. A nanopore is a small hole, of the order of 1 nanometer in diameter Immersion of a nanopore in a conducting fluid and application of a potential (voltage) across it results in a slight electrical current due to conduction of ions through the nanopore. The amount of current which flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore represents a reading of the DNA sequence. Nanopore sequencing technology is disclosed in U.S. Pat. Nos. 5,795,782, 6,015,714, 6,627,067, 7,238,485 and 7,258,838 and U.S. Pat Appln Nos. 2006003171 and 20090029477.

The isolated fragments may be sequenced directly or, in some embodiments, the released fragments may be amplified (e.g., by PCR) to produce amplification products that sequenced. In certain embodiments, amplification products may contain sequences that are compatible with use in, e.g., Illumina's reversible terminator method, Roche's pyrosequencing method (454), Life Technologies' sequencing by ligation (the SOLiD platform) or Life Technologies' Ion Torrent platform, as described above.

In certain embodiments, the sample sequenced may comprise a pool of nucleic acids from a plurality of samples, wherein the nucleic acids in the sample have a molecular barcode to indicate their source. In some embodiments the nucleic acids being analyzed may be derived from a single source (e.g., a single organism, virus, tissue, cell, subject, etc.), whereas in other embodiments, the nucleic acid sample may be a pool of nucleic acids extracted from a plurality of sources (e.g., a pool of nucleic acids from a plurality of organisms, tissues, cells, subjects, etc.), where by "plurality" is meant two or more. As such, in certain embodiments, a nucleic acid sample can contain nucleic acids from 2 or more sources, 3 or more sources, 5 or more sources, 10 or more sources, 50 or more sources, 100 or more sources, 500 or more sources, 1000 or more sources, 5000 or more sources, up to and including about 10,000 or more sources. Molecular barcodes may allow the sequences from different sources to be distinguished after they are analyzed.

The method described above may be used to isolate endogenous DNA from a variety of different samples, which endogenous DNA can be genotyped, e.g., sequenced, to investigate the individual from which the sample was obtained. For example, the method can be used to isolate fragments that represent at least 10%, at least 30%, at least 50%, or at least 70% or more of a genome of an individual, and the fragments can be sequenced and, optionally, compared to the genome of the reference sample.

In some cases, the method described above may be used in the analysis of a forensic sample, e.g., to identify humans through DNA analysis. As used herein, "forensics" is the study of evidence, for example, that discovered at a crime or accident scene that is then used in a court of law. "Forensic science" is any science used to answer questions of interest to the legal system, in particular the criminal or civil justice system, providing impartial scientific evidence for use in the courts of law, for example, in criminal investigations and trials. Forensic science is a multidisciplinary subject, drawing principally from chemistry and biology, but also from physics, geology, psychology and social science, for example. The goal of one aspect of human forensics, forensic DNA typing, is to determine the identity or genotype of DNA acquired from a forensic sample, for example, evidence from a crime scene or DNA sample from an individual. Typical sources of such DNA evidence include hair, bones, teeth, and body fluids such as saliva, semen, and blood. There often exists a need for rapid identification of a large number of humans, human remains and/or biological samples. Such remains or samples may be associated with war-related casualties, aircraft crashes, and acts of terrorism, for example.

Kits

Also provided by this disclosure are kits that contain reagents for practicing the subject methods, as described above. The subject kits contain at least: a) a universal adaptor (which may comprise a 5' T overhang); c) a library comprising fragmented human genomic DNA that has been ligated to an RNA promoter adaptor or a library of affinity-tagged transcripts made from the same; d) RNA oligonucleotides that are complementary to or have the same sequence as a sequence in the universal adaptor, or DNA oligonucleotides for making the same by in vitro transcription. If the kit does not contain the library of affinity-tagged transcripts, the kit may contain: e) a DNA-dependent RNA polymerase that primes RNA synthesis from the RNA promoter; f) a ribonucleotide mix that comprises an affinity-tagged ribonucleotide (e.g., biotin-UTP); and g) a substrate, e.g., beads, comprising a capture agent for the affinity tag.

The kit may optionally contain other components, for example: ligase, polymerase (e.g., a DNA polymerase such as Taq polymerase and an RNA polymerase such as T7 RNA polymerase), nucleotides, buffers, hybridization reagents, e.g., reagents for performing PERT or osPERT, etc. The various components of the kit may be present in separate containers or certain compatible components may be pre-combined into a single container, as desired.

In addition to above-mentioned components, the subject kits may further include instructions for using the components of the kit to practice the subject methods, i.e., instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging), etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

Aspects of the present teachings can be further understood in light of the following examples, which should not be construed as limiting the scope of the present teachings in any way.

In the present study, we use a method we call whole-genome in-solution capture (WISC) as an unbiased means to increase the proportion of endogenous DNA in aDNA sequencing libraries. To target as much of the remaining endogenous DNA as possible, we created human genomic DNA "bait" libraries from a modern reference individual with adapters containing T7 RNA polymerase promoters (see Material and Methods). We then performed in vitro transcription of these libraries with biotinylated UTP, producing RNA baits covering the entire human genome. The baits were hybridized to aDNA libraries in solution and pulled down with magnetic streptavidin-coated beads. The unbound, predominantly nonhuman DNA was then washed away, and the captured endogenous human DNA was eluted and amplified for sequencing. FIG. 1 shows a schematic overview of the WISC process, including the creation of the RNA bait libraries. By using both baits and adaptor-blocking oligos made from RNA, we were able to remove any residual baits and blockers by RNase treatment prior to PCR amplification.

Materials and Methods

Ancient Specimens

The four Bulgarian teeth used in this study were obtained from four different excavations.

Sample P192-1 was found at the site of a pit sanctuary near Svilengrad, Bulgaria, excavated between 2004 and 2006. The pits are associated with the Thracian culture and date to the Early Iron Age (800-500 BC) based on pottery found in the pits. A total of 67 ritual pits, including 16 pits containing human skeletons or parts of skeletons, were explored during the excavations. An upper wisdom tooth from an adult male was used for DNA analysis.

Sample T2G2 was found in a Thracian tumulus (burial mound) near the village of Stambolovo, Bulgaria. Two small tumuli dating to the Early Iron Age (850-700 BC) were excavated in 2008. A canine tooth from an inhumation burial of a child (c.12 years old) inside a dolium was used for DNA analysis.

Sample V2 was found in a flat cemetery dating to the Late Bronze Age (1500-1100 BC) near the village of Vratitsa, Bulgaria. Nine inhumation burials were excavated between 2003 and 2004. A molar from a juvenile male (age 16-17) was used for DNA analysis.

Sample K8 was found in the Yakimova Mogila Tumulus, which dates to the Iron Age (450-400 BC), near Krushare, Bulgaria. An aristocratic inhumation burial containing rich grave goods was excavated in 2008.

A molar from one individual, probably male, was used for DNA analysis.

Other specimens are as follows.

Sample M4 is an ancient hair sample obtained from the Borum Eshøj Bronze Age burial in Denmark. The burial comprised three individuals in oak coffins, commonly referred to as "the woman," "the young man," and "the old man." The M4 sample is from the latter. The site was excavated in 1871-1875 and the coffins dated to c.1350 BC.

Samples NA39-50 were obtained from pre-Columbian Chachapoyan and Chachapoya-*Inca* remains dating between 1000 and 1500 AD. They were recovered from the site Laguna de los Condores in northeastern Peru.

Bone samples were used for DNA analysis.

DNA Extraction and aDNA Library Preparation

All DNA extraction and initial library preparation steps (prior to amplification) were performed in the dedicated clean labs at the Centre for GeoGenetics in Copenhagen, Denmark, via established procedures to prevent contamination, including the use of indexed adapters and primers during library preparation.

The lab work was conducted over an extended time period and by a number of different researchers, which is why the exact protocols vary somewhat between samples.

Bulgarian Samples:

The surface of each tooth was wiped with a 10% bleach solution and then UV irradiated for 20 min. Part of the root was then excised and the inside of the tooth was drilled to produce approximately 200 mg of powder. DNA was isolated with a previously described silica-based extraction method.

The purified DNA was subjected to end repair and dA-tailing with the Next End Prep Enzyme Mix (New England Biolabs) according to the manufacturer's instructions. Next, ligation to Illumina PE adapters (Illumina) was performed by mixing 25 µl of the end repair/dA-tailing reaction with 1 µl of PE adapters (5 µM) and 1 µl of Quick T4 DNA Ligase (NEB). The mixture was incubated at 25° C. for 10 min and then purified with a QIAGEN MinElute spin column according to the manufacturer's instructions (QIAGEN). Finally, the libraries were amplified by PCR by mixing 5 µl of the DNA library template with 5 µl 10×PCR buffer, 2 µl MgCl2 (50 mM), 2 µl BSA (20 mg/ml), 0.4 µl dNTPs (25 mM), 1 µl each primer (10 µM, inPE+multiplex indexed), and 0.2 µl of Platinum Taq High Fidelity Polymerase (Invitrogen/Life Technologies). The PCR conditions were as follows: 94° C./5 min; 25 cycles of 94° C./30 s, 60° C./20 s, 68° C./20 s; 72° C./7 min. The resulting libraries were purified with QiaQuick spin columns (QIAGEN) and eluted in 30 µl EB buffer.

Peruvian Bone Samples:

DNA was isolated from seven bone samples via a previously described silica-based extraction method.

DNA was further converted into indexed Illumina libraries with 20 µl of each DNA extract with the NEBNext DNA Library Prep Master Mix Set for 454 (NEB) according to the manufacturer's instructions, except that SPRI bead purification was replaced by MinElute silica column purification (QIAGEN). Illumina multiplex blunt end adapters were used for ligation at a final concentration of 1.0 µM in a final volume of 25 µl. The Bst Polymerase fill-in reaction was inactivated after 20 min of incubation by freezing the sample. Library preparation was followed by a two-step PCR amplification Amplification of purified libraries was done with Platinum Taq High Fidelity DNA Polymerase (Invitrogen) with a final mixture of 10× High Fidelity PCR Buffer, 50 mM magnesium sulfate, 0.2 mM dNTP, 0.5 µM Multiplexing PCR primer 1.0, 0.1 µM Multiplexing PCR primer 2.0, 0.5 µM PCR primer Index, 3% DMSO, 0.02 U/µl Platinum Taq High Fidelity Polymerase, 5 µl of template, and water to 25 µl final volume. Three PCR reactions were done for each library with the following PCR conditions: a 3 min activation step at 94° C., followed by 14 cycles of 30 s at 94° C., 20 s at 60° C., 20 s at 68° C., with a final extension of 7 min at 72° C. All three reactions per library were purified with QIAGEN MinElute columns and pooled into one single reaction. A second PCR was performed with the same conditions as before but with 22 cycles. One reaction per library was then performed with 10 µl from the purified pool of the three previous reactions. Libraries were run on a 2% agarose gel and gel purified with a QIAGEN gel extraction kit according to the manufacturer's instructions.

Danish Hair Sample:

DNA was extracted from 70 mg of hair with phenol-chloroform combined with MinElute columns from QIAGEN as previously described.

While fixed on silica filters, the DNA was purified sequentially with AW1/AW2 wash buffers (QIAGEN Blood and Tissue Kit), Salton buffer (MP Biomedicals), and PE buffer, before being eluted in 60 µl EB buffer (both QIAGEN). Then, 20 µl of DNA extract was built into a blunt-end NGS library with the NEBNext DNA Sample Prep Master Mix Set 2 (E6070) and Illumina specific adapters. The libraries were prepared according to manufacturer's instructions, with a few modifications outlined below. The initial nebulization step was skipped because of the fragmented nature of ancient DNA. End-repair was performed in 25 µl reactions with 20 µl of DNA extract. This was incubated for 20 min at 12° C. and 15 min at 37° C. and purified with PN buffer with QIAGEN MinElute spin columns and eluted in 15 µl. After end-repair, Illumina-specific adapters were ligated to the end-repaired DNA in 25 µl reactions. The reaction was incubated for 15 min at 20° C. and purified with PB buffer on QIAGEN MinElute columns before being eluted in 20 µl EB Buffer. The adaptor fill-in reaction was performed in a final volume of 25 µl and incubated for 20 min at 37° C. followed by 20 min at 80° C. to inactivate the Bst enzyme. The entire DNA library (25 µl) was then amplified and indexed in a 50 µl PCR reaction, mixing with 5 µl 10×PCR buffer, 2 µl MgSO4 (50 min), 2 µl BSA (20 mg/ml), 0.4 µl dNTPs (25 min), 1 µl of each primer (10 µM, inPE forward primer+multiplex indexed reverse primer), and 0.2 µl Platinum Taq High Fidelity DNA Polymerase (Invitrogen). Thermocycling was carried out with 5 min at 95° C., followed by 25 cycles of 30 s at 94° C., 20 s at 60° C., and 20 s at 68° C., and a final 7 min elongation step at 68° C. The amplified library was then purified with PB buffer on QIAGEN MinElute columns, before being eluted in 30 µl EB.

Preparation of RNA Bait Libraries

Creation of Human Genomic DNA Libraries with T7 Adapters:

Five micrograms of human DNA (HapMap individual NA21732, a Masai male) was sheared on a Covaris S2 instrument with the following conditions: 8 min at 10% duty cycle, intensity 5, 200 cycles/burst, frequency sweeping. The resulting fragmented DNA (~150-200 bp average size, range 100-500) was subjected to end repair and dA-tailing by a KAPA library preparation kit (KAPA) according to the manufacturer's protocol. Ligation was also performed with this kit, but with custom adapters. T7 adaptor oligos 1 and 2 (5'-GATCTTAAGGCTAGAGTACTAATACGACTCACT ATAGGG*T-3' (SEQ ID NO:1) and 5'-P-CCCTATAGT-GAGTCGTATTAGTACTCTAGCCTTAAGATC-3' (SEQ ID NO:2)) were annealed by mixing a 12.5 µl of each 200 µM oligo stock with 5 µl of 10× buffer 2 (NEB) and 20 µl of H$_2$O. This mixture was heated to 95° C. for 5 min, then left on the bench to cool to room temperature for approximately 1 hr.

One microliter of this T7 adaptor stock was used for the ligation reaction, again according to the library preparation kit instructions (KAPA). The libraries were then size selected on a 2% agarose gel to remove unligated adapters and select for fragments ~200-300 bp in length (inserts ~120-220 bp). After gel extraction with a QIAquick Gel Extraction kit (QIAGEN), the libraries were PCR amplified in four separate reactions with the following components: 25 µl 2× HiFi HotStart ReadyMix (KAPA), 20 µl H$_2$O, 5 µl PCR primer (5'-GATCT-TAAGGCTAGAGTACTAATACGACTCACTATAGGG*T-3', same as T7 oligo 1 above, 10 µM stock), and 5 µl purified ligation mix. The cycling conditions were as follows: 98° C./1 min, 98° C./15 s; 10 cycles of 60° C./15 s, 72° C./30 s; 72° C./5 min. The reactions were pooled and purified with AMPure XP beads (Beckman Coulter), eluting in 25 µl H$_2$O.

In Vitro Transcription of Bait Libraries:

To transcribe the bait libraries into biotinylated RNA, we assembled the following in vitro transcription reaction mixture: 5 µl amplified library (~500 ng), 15.2 µl H2O, 10 µl 5×NASBA buffer (185 min Tris-HCl [pH 8.5], 93 min MgCl2, 185 min KCl, 46% DMSO), 2.5 µl 0.1 M DTT, 0.5 µl 10 mg/ml BSA, 12.5 µl 10 min NTP mix (10 min ATP, 10 min CTP, 10 min GTP, 6.5 min UTP, 3.5 min biotin-16-UTP), 1.5 µl T7 RNA Polymerase (20 U/µl, Roche), 0.3 µl Pyrophosphatase (0.1 U/µl, NEB), and 2.5 µl SUPERase-In RNase inhibitor (20 U/µl, Life Technologies). The reaction was incubated at 37° C. overnight, treated for 15 min at 37° C. with 1 µl TURBO DNase (2 U/µl, Life Technologies), and then purified with an RNeasy Mini kit (QIAGEN) according to the manufacturer's instructions, eluting twice in the same 30 µl of $H_2O$. A single reaction produced ~50 µg of RNA. The size of the RNA was checked by running ~100 ng on a 5% TBE/Urea gel and staining with ethidium bromide. For long-term storage, 1.5 µl of SUPERase-In was added, and the RNA was stored at −80° C.

Preparation of RNA Adaptor-Blocking Oligos

All of the aDNA libraries that we used for testing the enrichment protocol contained indexed multiplex adapters (see "DNA Extraction and Library Preparation" above). To block these sequences and prevent nonspecific binding during capture, we created adaptor-blocking RNA oligos, which can be produced in large amounts and are easy to remove by RNase treatment when capture is complete. The following oligonucleotides were annealed as described above: T7 universal promoter (5'-AGTACTAATACGACTCAC-TATAGG-3' (SEQ ID NO:3))+either Multiplex-block-P5 (5'-AGATCGGAAGAGCGTCGTGTAGG-GAAAGAGTGTAGATCTCGGTGGTCGCCGTAT CAT-TCCTATAGTGAGTCGTATTAGTACT-3' (SEQ ID NO:4)) or Multiplex-block-P7 (5'-AGATCG-GAAGAGCACACGTCTGAACTCCAGTCACNNNNN-NATCTCGTATGCCGT CTTCTGCTTGCCTATAGT-GAGTCGTATTAGTACT-3' (SEQ ID NO:5)), the latter containing random nucleotides at the site of the index sequence, which allows the same adaptor-blocking oligos to be used for all libraries.

For each of these double-stranded oligonucleotide solutions, 700 ng was subjected to in vitro transcription with a T7 High-Yield RNA Synthesis kit (NEB) according to the manufacturer's instructions. After treatment with 1 µl of TURBO DNase (37° C./15 min), the RNA was purified with an RNeasy Mini kit according to the manufacturer's instructions, except that 675 µl of ethanol (instead of 250 µl) was added at step 2 of the protocol to ensure the retention of small RNAs. The RNA was eluted in 30 µl $H_2O$, to which 1.5 µl of SUPERase-In was added prior to storage at −80° C.

DNA Capture

Hybridization

For the ancient DNA "pond" (the mixture to which the RNA bait will be hybridized), 27 µl of each aDNA library (81-550 ng depending on the library) was mixed with 2.5 µl human Cot-1 DNA (1 mg/ml, Life Technologies) and 2.5 µl salmon sperm DNA (10 mg/ml, Life Technologies) in 200 µl PCR tubes. The RNA baits and adaptor-blocking oligos were mixed in a separate 1.5 ml tube as follows: for each capture, 1 µl (500 ng) biotinylated RNA bait library, 3 µl SUPERase-In, 2 µl P5 multiplex block RNA (100 µM stock, see above), and 2 µl P7 multiplex block RNA (100 µM stock, see above). The DNA pond was heated in a thermal cycler to 95° C. for 5 min, followed by 65° C. for 5 min. When the DNA had been at 65° C. for 2.5 min, the RNA bait mix was heated to 65° C. for 2.5 min in a heat block. After the pond DNA had been at 65° C. for 5 min, 26 µl of prewarmed hybridization buffer (10×SSPE, 10×Denhardt's, 10 min EDTA, 0.2% SDS, and 0.01% Tween 20) was added, followed by 8 µl RNA bait/block mix to produce a 66 µl total reaction. The reaction was mixed by pipetting, then incubated at 65° C. for ~66 hr.

Pulldown

For each capture reaction, 50 µl of Dynabeads MyOne Streptavidin C1 beads (Life Technologies) was mixed with 200 µl bead wash buffer (1 M NaCl, 10 min Tris-HCl [pH 7.5], 1 min EDTA, and 0.01% Tween 20), vortexed for 30 s, then separated on a magnetic plate for 2 min before supernatant was removed. This wash step was repeated twice and after the last wash the beads were resuspended in 134 µl bead wash per sample. Next, 134 µl of bead solution was added to the 66 µl DNA/RNA hybridization mix, the solution was vortexed for 10 s, and the mix was incubated at room temperature for 30 min, vortexing occasionally. The mixture was then placed on a magnet to separate the beads and the supernatant was removed. The beads were incubated in 165 µl low-stringency buffer (lx SSC/0.1% SDS/0.01% Tween 20) for 15 min at room temperature, followed by three 10 min washes at 65° C. in 165 µl prewarmed high-stringency buffer (0.1×SSC/0.1% SDS/0.01% Tween 20). Hybrid-selected DNA was eluted in 50 µl of 0.1 M NaOH for 10 min at room temperature, then neutralized by adding 50 µl 1 M Tris-HCl (pH 7.5). Finally, the DNA was concentrated with 1.8× AMPure XP beads, eluting in 30 µl $H_2O$.

Amplification

The captured pond was PCR amplified by combining the 30 µl of captured DNA with 50 µl 2×NEB Next Master Mix, 0.5 µl each primer (200 µM stocks of primer P5, 5'-AAT-GATACGGCGACCACCGA-3' (SEQ ID NO:6), and P7, 5'-CAAGCAGAAGACGGCATACGA-3' (SEQ ID NO:7)), 0.5 µl RNase A (7,000 U/ml, QIAGEN), and 18.5 µl $H_2O$. Cycling conditions were as follows: 98° C./30 s; 15-20 cycles of 98° C./10 s, 60° C./30 s, 72° C./30 s; 72° C./2 min. The reactions were purified with 1.8× (180 µl) AMPure XP beads and eluted in 30 µl $H_2O$.

Library Pooling and Multiplex Sequencing

Captured libraries were pooled in equimolar amounts (determined by analysis on an Agilent Bioanalyzer 2100) and sequenced on either a MiSeq (postcapture Bulgarian libraries, 2×150 bp reads) or HiSeq (precapture Bulgarian libraries (2×90 bp reads) and all other libraries (2×101 bp reads). For the postcapture libraries, 10% PhiX (a viral genome with a balanced nucleotide representation) was spiked in to compensate for the low complexity of the libraries, which can cause problems with cross-talk matrix calculation, cluster identification, and phasing during the sequencing run.

Mapping and Data Analysis

Prior to mapping, paired-end reads were merged and adapters were trimmed with the program SeqPrep with default settings, including a length cutoff of 30 nt. The merged reads and trimmed unmerged reads were mapped separately to the human reference genome (UCSC Genome Browser hg19) with BWA v.0.5 with seeding disabled (−1 1000). Duplicates were then removed from the combined bam file with samtools (v.0.1.18) and reads were filtered for mapping qualities ≥30.

For the postcapture libraries, we noted that there were a small number of fragments with the exact same lengths and mapping coordinates (primarily mapping to the mtDNA) in multiple libraries. Because we performed the captures and amplifications separately for each library prior to sequencing, the most parsimonious explanation for this observation is that the high clonality of the libraries led to mixed clusters on the sequencer and some misassignments of index sequences, despite the spike-in of PhiX described above. This phenomenon has been previously reported for multiplexed libraries and is probably exacerbated by high levels of clonality.

To correct for this issue, any potentially cross-contaminating fragments (defined as those with the same lengths and mapping coordinates in more than one library) were removed bioinformatically with an in-house bash script and BEDTools.

For downsampling experiments, the initial fastq file was reduced to the desired number of reads and then the reads were mapped as described above. Overlap between the pre- and postcapture libraries was assessed with BEDTools. Coverage plots were created with Integrative Genomics Viewer. DNA damage tables were generated with mapDamage 2.0.30

Overlap with repetitive regions of the genome was determined by intersecting with the RepeatMasker table for hg19 (UCSC Genome Browser) via BEDTools. For mtDNA haplogroup assignments, all trimmed and merged reads were separately aligned to the revised Cambridge reference sequence (rCRS) with the same pipeline described above for the full genome. Mutations were identified with MitoBamAnnotator and haplogroups were assigned with mthap v.0.19a based on PhyloTree Build. Sex identification was performed with a previously published karyotyping tool for shotgun sequencing data.

Variant Calling and Principal Component Analysis

For variant calling, sites were overlapped with SNPs from the 1000 Genomes Project Phase 1 data set (v.3), filtering for base qualities ≥30 in the ancient samples and removing related individuals from 1000 Genomes. For PCAs with Native Americans, low-coverage sequenced genomes from ten additional individuals (Mayan individuals HGDP00854, HGDP00855, HGDP00856, HGDP00857, HGDP00860, HGDP00868, HGDP00877; Karitiana individuals HGDP00998 and BI16; and Aymara individual TA6) were also included in the intersection. Because of low coverage in the ancient samples, most positions were covered by 0 or 1 read; for positions covered by more than one read, a random read was sampled and the site was made homozygous. For PCA analysis, SNPs were filtered for minor allele frequencies ≥5% and PCAs were constructed with smartpca. Principal components were computed with only the modern samples, and the ancient individual was then projected onto the PCA. PCA plots were created with R v.2.14.2.

Results

WISC was tested on 12 human aDNA libraries derived from non-frozen-preserved specimens: four Iron and Bronze Age human teeth from Bulgaria, seven pre-Columbian human mummies from Peru, and one Bronze Age human hair sample from Denmark. The DNA was extracted and the libraries built in a dedicated clean room (see Material and Methods). Shotgun sequencing prior to capture indicated that all libraries contained low levels of endogenous DNA (average 1.2%, range 0.04%-6.2%; see FIG. 4). To allow for direct comparison, the numbers of reads in the pre- and postcapture libraries were adjusted to be equal prior to mapping by taking the first n reads from the respective raw fastq files (FIG. 4). In the case of the hair and bone libraries, the results for 1 million reads are shown for ease of comparison with the tooth libraries. Prior to mapping, the paired-end reads were merged where possible, any remaining adaptor sequence was trimmed from the merged and unmerged reads, and reads containing only adaptor sequence (i.e., adaptor dimers) were discarded. As shown in FIG. 4, whole-genome capture decreased the number of reads discarded at this step, reducing the sequencing capacity taken up by these uninformative sequences, which are common contaminants in aDNA sequencing libraries.

After capture, enrichments were observed ranging from 6-fold to 159-fold for number of reads mapping to the human genome at MAPQ≥30, resulting in 1.6%-59.2% of reads mapping after capture. For unique fragments, we observed enrichments of 2-fold to 13-fold (FIG. 4); however, the fraction of unique reads changes with different amounts of sequencing and also is sensitive to the level of complexity of the original library (FIGS. 2A and 2B). The level of enrichment was negatively correlated with the amount of endogenous DNA present in the precapture library—the higher the amount prior to capture, in general, the lower the degree of enrichment (e.g., samples P192-1 and NA42; see FIG. 4). This phenomenon has previously been observed for the enrichment of pathogen DNA in clinical samples.

The number of unique reads increased in all cases; however, even after sequencing of 1 million reads, most of the unique molecules in the postcapture libraries had already been observed, as evidenced by the high levels of clonality (66%-96%) in these libraries. We generally captured a large proportion (15%-90%) of the endogenous fragments observed in the precapture libraries (FIG. 4). This number also increased with additional sequencing (see FIG. 2C and discussion below). We observed only a slight increase in the percent of fragments falling within known repetitive regions of the genome (FIG. 4), with the average increasing from 36% precapture to 39% postcapture. There was no obvious correlation with the amount of starting DNA in the sample. Thus, at least for libraries containing very low levels of endogenous DNA, biased enrichment of repetitive sequences does not appear to be a problem. In the postcapture libraries, the unmapped fraction had a similar composition of environmental (primarily bacterial) sequences to the precapture library (data not shown).

Importantly for aDNA studies, which have historically relied on identifying mtDNA haplogroups from ancient samples, >1× coverage of the mtDNA was achieved with 1 million reads for 5 of the 12 postcapture libraries (FIG. 4). For these five samples, we were able to tentatively call mtDNA haplogroups. Intersection with the 1000 Genomes Project reference panel demonstrated that capture increased the number of unique SNPs between 2- and 14-fold (FIG. 4), increasing the resolution of principal component analysis plots involving these individuals (see Discussion below). We did not observe any bias in X chromosome capture resulting from the use of a male Masai individual (NA21732) for the capture probes: the proportion of reads mapped to the X chromosome remained approximately the same before and after capture (Table S2). Furthermore, for the 17 total SNPs that changed alleles between the eight pre- and postcapture libraries sequenced to higher levels (0-6 SNPs per sample), only ten SNPs changed from not matching to matching NA21732 after capture (Table S3). Thus, at least for modern humans, divergence between the probe and target on the population level does not appear to produce significant allelic bias in the postcapture library. However, it is possible that more noticeable effects could be seen for indels or copy number variants if high enough coverage were obtained.

To determine how many new unique fragments are discovered with increasing amounts of sequencing, we sequenced the hair and bone libraries to higher coverage (~8-18 million reads via multiplexed Illumina HiSeq sequencing). FIGS. 2A and 2B show the results of increasing levels of sequencing of libraries NA40 (Peruvian bone) and M4 (Danish hair), which are generally representative of the patterns we saw for the remaining six libraries (see Figure S1). For NA40, although the yield of unique fragments from the precapture library increased in a linear manner, the yield from the postcapture library increased rapidly with initial sequencing and began to plateau after approximately four million reads (FIG. 2A). Similarly, there was a rapid initial increase in unique fragments up to approximately five million reads sequenced for both the pre- and postcapture M4 libraries; this increase then slowed with sequencing up to 18.7 million reads (FIG. 2B). The results from the remaining six libraries are shown in FIG. 51. These plots also demonstrate that the fold enrichment in unique reads decreases with increasing amounts of sequencing (FIGS. 2A, 2B, and S1), as the precapture library begins to be sampled more exhaustively. Thus, WISC allowed us to access the majority of unique reads present in the postcapture library with even low levels of sequencing, such as those obtainable with a single run on an Illumina MiSeq.

Figure 2E:
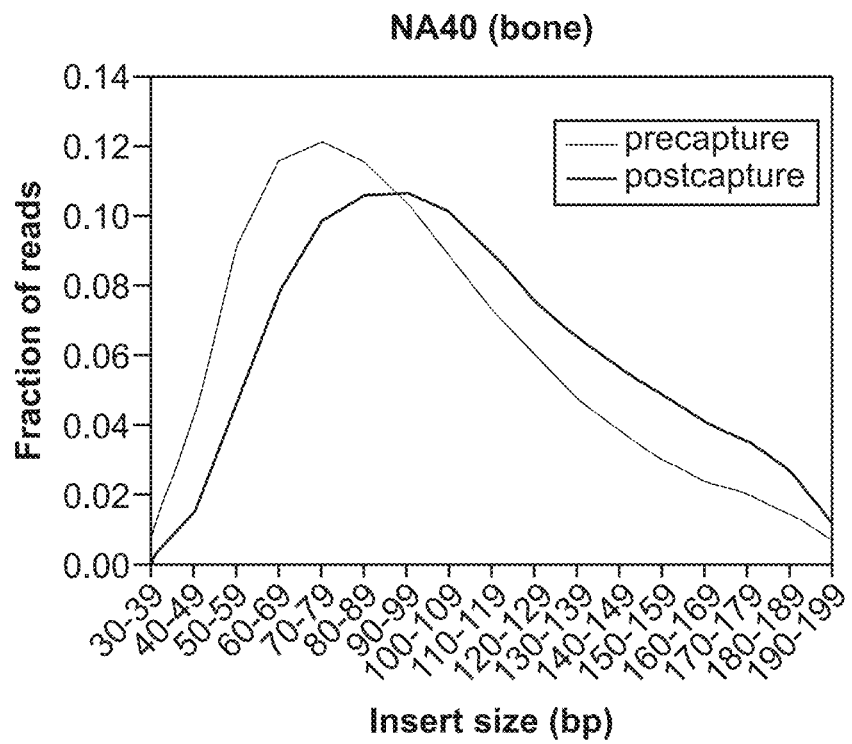
Figure 2F:
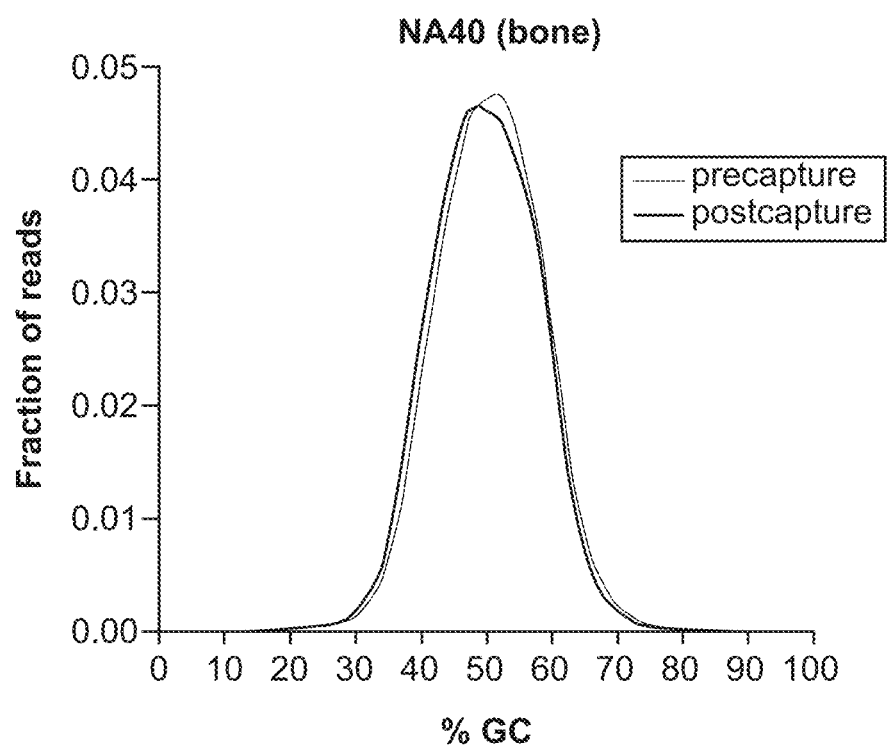

The efficiency of endogenous molecule capture in the precapture library was measured with higher levels of sequencing. As shown in FIG. 2C, for library NA40, 77% (53,524) of unique fragments in the precapture library were also sequenced in the postcapture library with 12,285,216 reads sequenced; note that this fraction was 42% for 1 million reads sequenced (FIG. 4). Furthermore, an additional 136,978 unique fragments were sequenced after capture with the same amount of sequencing (FIG. 2C). These fragments were generally evenly distributed across the genome; FIG. 2D shows a coverage plot for libraries M4 and NA40 at a random 10 Mb region of chromosome 1. The size of the fragments in the postcapture libraries tended to be slightly larger (FIG. 2E), probably because of the stringency of the hybridization and wash steps—which could be decreased but would, we predict, result in lower levels of enrichment—and some loss during purifications, resulting in the preferential retention of longer fragments. Because aDNA is highly fragmented compared to modern contaminants, we tested whether the overall DNA damage patterns (an increase in C-to-T and G-to-A transitions at the ends of fragments, diagnostic of ancient DNA) also changed with the change in fragment size after capture. We observed that the overall DNA damage patterns remained similar in the pre- and postcapture libraries (Table S4), both for the libraries as a whole and when they were partitioned by size (<70 bp and >70 bp). The patterns for libraries V2, K8, and M4 are not typical of ancient DNA, possibly because of favorable preservation conditions, sample contamination prior to capture, or both (Table S4). Finally, the GC content of reads in the postcapture library was slightly decreased (FIG. 2F), as previously observed for in-solution exome capture.

Figure 3A:
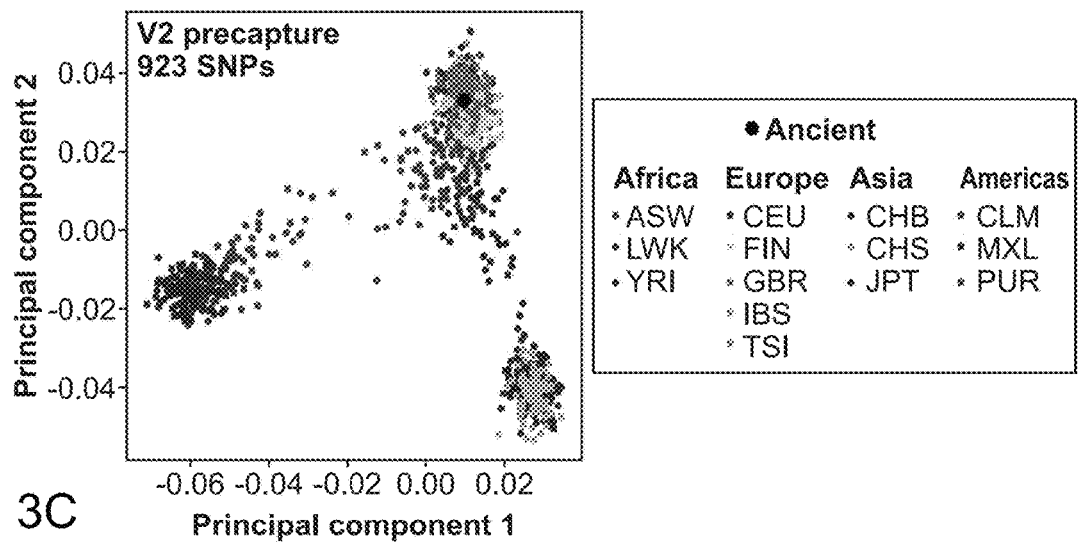
FIG. 3A-3F shows the results of principal component analysis of pre- and post-capture samples based on sequencing one million reads each. Principal component analysis of SNPs overlapping between the 1000 Genomes reference panel and each ancient individual, with Native American individuals also included in (FIG. 3E) and (FIG. 3F). The principal components were calculated with the modern individuals only, and the ancient individual was then projected onto the plot. Shown are (FIG. 3A) V2 (Bulgarian tooth) precapture and (FIG. 3B) postcapture.
Figure 3C:
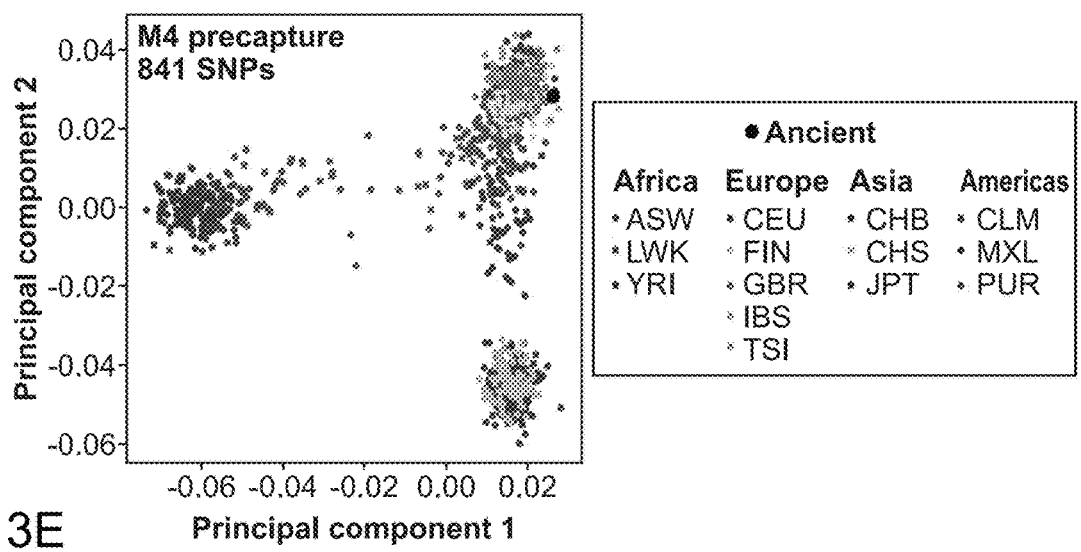
Figure 3E:
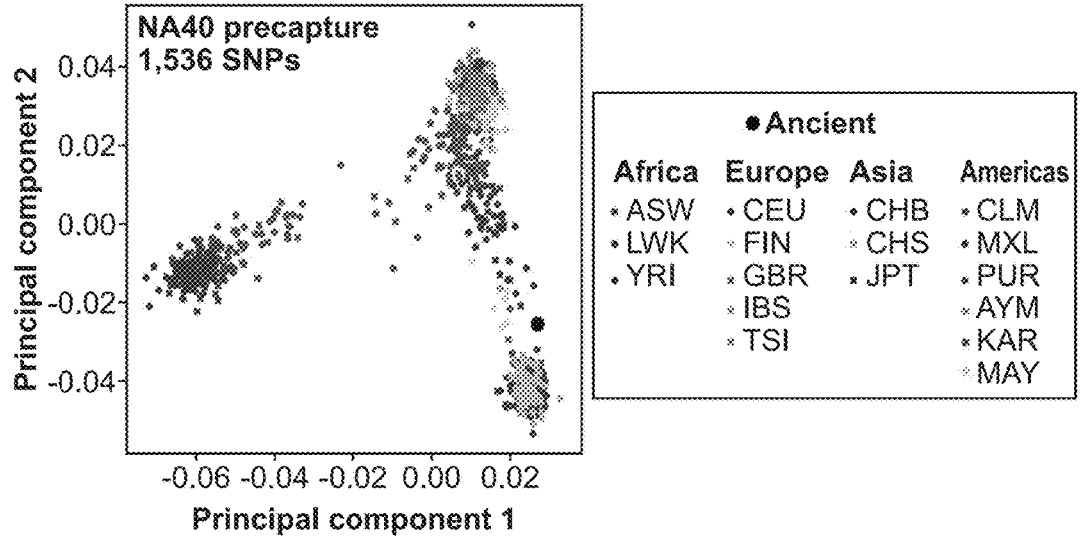
Figure 3B:
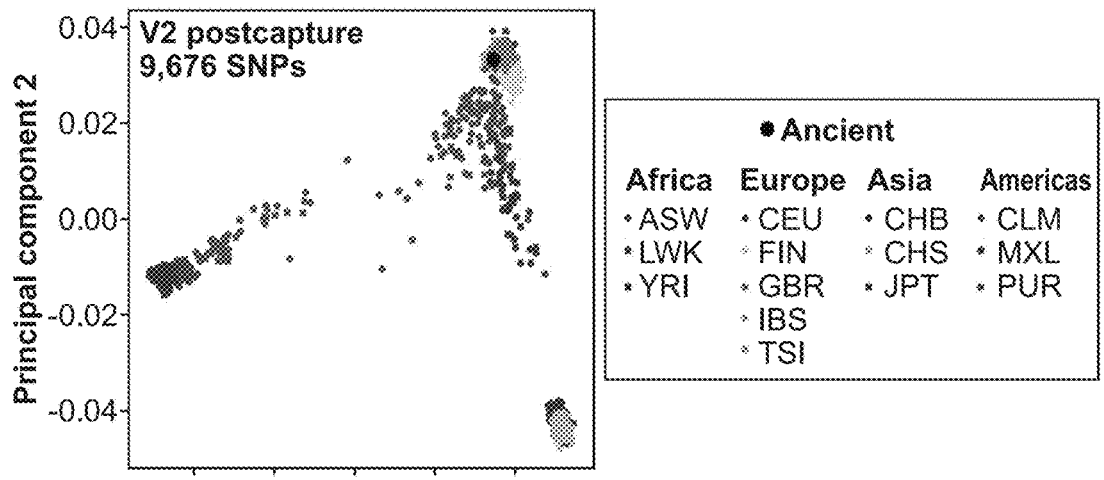
Figure 3D:
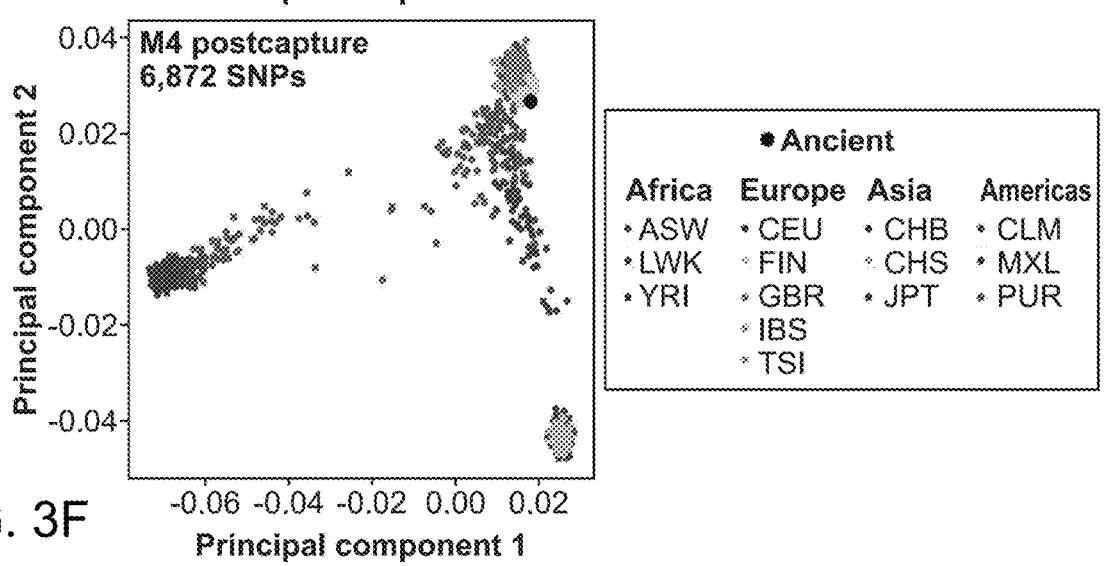
Figure 3F:
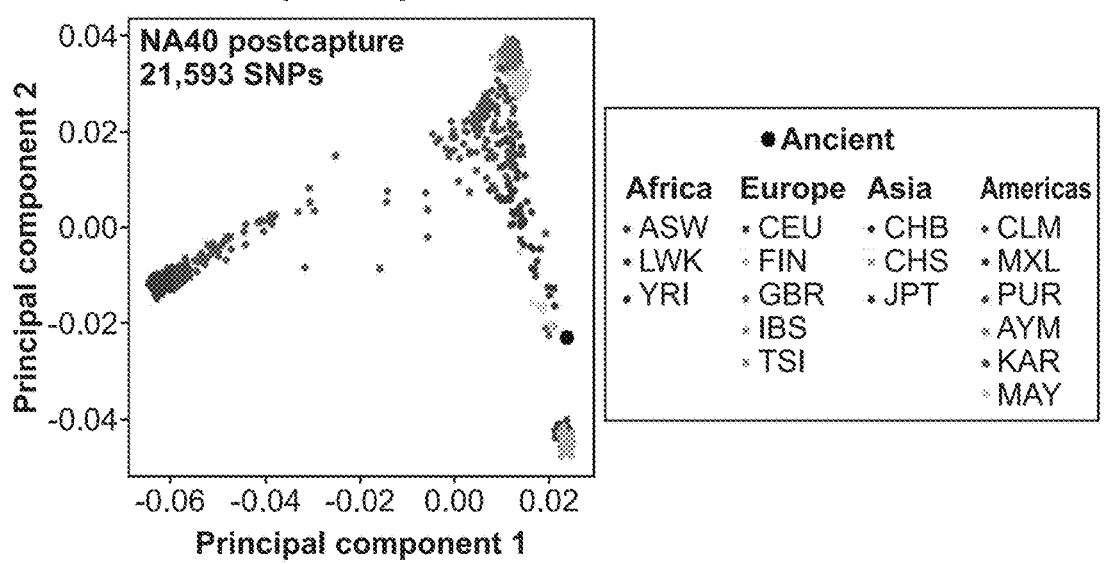

The ultimate goal of sequencing DNA from ancient samples is usually to identify informative variation for population genetics analyses. We used the SNPs identified by intersections with the 1000 Genomes reference panel (see FIG. 4 and discussion above) to perform principal component analysis (PCA). Only SNPs with a minor allele frequency ≥5% were used for this analysis. FIG. 3 shows the pre- and postcapture PCAs for samples V2 (Bulgarian), M4 (Danish hair), and NA40 (Peruvian mummy). As expected, the two European samples fell into the European clusters on the PCA both before capture (FIGS. 3A and 3C) and after capture (FIGS. 3B and 3D). However, the increased number of SNPs after capture allows for improved resolution of the subcontinental affiliation of each ancient sample (FIGS. 3B and 3D). PCAs with only the European populations in 1000 Genomes further resolve the placement of some of these samples after capture (Figure S3). For the Peruvian mummies, we also included 10 Native American individuals from Central and South America in the PCA (FIGS. 3E and 3F). Interestingly, all of the mummies fell between the Native American populations (KAR, MAY, AYM) and East Asian populations (JPT, CHS, CHB), as would be expected for a nonadmixed Native American individual (FIGS. 3E, 3F, and S2). These mummies belonged to the pre-Columbian Chachapoya culture, who, by some accounts, were unusually fair-skinned, suggesting a potential for pre-Columbian European admixture. However, based on our preliminary results, these individuals appear to have been ancestrally Native American.

A whole-genome in-solution capture method, WISC, has been developed that can be used to highly enrich the endogenous contents of aDNA sequencing libraries, thus reducing the amount of sequencing required to sample the majority of unique fragments in the library. Previous methods for targeted enrichment of aDNA libraries have focused only on a subset of the genome (e.g., the mitochondrial genome, a single chromosome, or a subset of SNPs). Although these methods have generated useful information while reducing sequencing costs, they all involve discarding a large proportion of potentially informative sequences, often from samples that already contain a reduced representation of the genome. Excluding initial library costs (which are the same for all methods) and sequencing, the cost to perform WISC is approximately S50/sample, primarily because of the cost of the streptavidin-coated beads used for capture. In contrast, in-solution exome capture via a commercial kit is approximately 1,000/sample, and we calculate the previously reported chromosome 21 capture method to have an initial cost of approximately 55,000 (to purchase the nine one-million-feature DNA arrays used to generate the RNA probes), plus a cost of ~50/sample for the actual capture experiments. Finally, if one desired to array-synthesize probes tiled across the entire genome—i.e., a similar approach to the chromosome 21 capture but for the whole genome—we calculate that it would cost ~$300,000-$400,000 to purchase the necessary arrays. All of these methods would reduce sequencing costs to a large extent compared to sequencing the precapture library, but, as noted above, several do so at the cost of discarding potentially informative sequences.

Our test libraries, like many aDNA libraries created from similar specimens, did not contain sufficient endogenous DNA to cover the entire genome, making it impossible to call genotypes for these samples; indeed, >99.9% of sites were covered by 0 or 1 read. Identifying SNPs from these samples is further complicated by the presence of DNA damage, specifically C-to-T and G-to-A transitions. Thus, in order to more confidently identify SNPs, we intersected our data set with a list of known SNPs from the 1000 Genomes reference panel. The likelihood that a damaged SNP will be found at the exact same position and with a matching allele as a SNP from the reference set is quite low, and thus we were able to leverage the identified SNPs to perform informative population genetics analyses without filtering out large subsets of the data (FIG. 3)

It should be noted that a reference panel, preferably with full genome sequence data (although this is not essential), is required for this type of analysis of poorly preserved specimens with low levels of genome coverage. However, because WISC reduces the required amount of sequencing required per library, multiple individuals from the same population can be analyzed, a key consideration for studies focusing on the spatial and temporal distribution of ancient populations.

As shown in FIG. 4, >1× coverage of the mtDNA was obtained for five of the libraries. This number is lower than the typical enrichment achieved when targeting the mtDNA alone via capture, but this is not surprising given that a wider range of sequences is being targeted. A similar phenomenon was observed in the capture of nuclear and organellar DNA from ancient maize. mtDNA haplogroups could be tentatively called for these samples. The two Bulgarian Iron Age individuals (P192-1 and T2G5) fell into haplogroups U3b and HV(16311), respectively. Haplogroup U3 is especially common in the countries surrounding the Black Sea, including Bulgaria, and in the Near East, and HV is also found at low frequencies in Europe and peaks in the Near East.

The three Peruvian mummies fell into haplogroups B2, M (an ancestor of D), and D1, all derived from founder Native American lineages and previously observed in both pre-Columbian and modern populations from Peru. In these experiments, capture yield was limited by the degree of complexity of the starting libraries and could potentially be increased by improved aDNA extraction and library preparation methods.

Finally, because it is not necessary to design an array for this method (i.e., a sequenced genome is not required), WISC could also be used to capture DNA from specimens of extinct species by creating baits from the genome of an extant relative. The effect of sequence divergence between species on capture efficiency remains to be determined, but chimpanzee-targeted probes have successfully been used to capture human and gorilla sequences.

In addition, WISC has applications in other contexts, such as the enrichment of DNA in forensic, metagenomic, and museum specimens.

It will also be recognized by those skilled in the art that, while the invention has been described above in terms of preferred embodiments, it is not limited thereto. Various features and aspects of the above described invention may be used individually or jointly. Further, although the invention has been described in the context of its implementation in a particular environment, and for particular applications (e.g. ancient DNA analysis) those skilled in the art will recognize that its usefulness is not limited thereto and that the present invention can be beneficially utilized in any number of environments and implementations where it is desirable to reduce sequencing reads to obtain a desired number of unique targeted DNA fragments. Accordingly, the claims set forth below should be construed in view of the full breadth and spirit of the invention as disclosed herein.

What is claimed is:

1. A method for capturing DNA molecules in solution, comprising:
   (a) ligating a universal adaptor to DNA that has been extracted from a sample;
   (b) hybridizing the extracted DNA, in solution, with
       (i) affinity-tagged RNA probes generated by: in vitro transcribing, in the presence of an affinity-tagged ribonucleotide, a library of DNA molecules that have been ligated to an adapter that comprises an RNA promoter; and
       (ii) RNA oligonucleotides that are complementary to at least some of the sequence of the universal adaptor and block hybridization to the universal adaptor;
   (c) binding the product of step (b) with a capture agent that is tethered to a substrate, thereby capturing the hybridized DNA molecules on the substrate;
   (d) washing the substrate to remove any unbound DNA molecules;
   (e) treating the substrate with an RNAse to simultaneously (i) degrade the RNA oligonucleotides and (ii) release the captured DNA molecules from the support by degrading the RNA probes; and
   (f) amplifying the released DNA molecules after step (e) by PCR (polymerase chain reaction) using a primer pair that comprises a primer that hybridizes to the universal adaptor.

2. The method of claim 1, wherein the sample is a sample of tooth, bone, nail or hair.

3. The method of claim 1, wherein the sample is a clinical, forensic, archaeological or environmental sample.

4. The method of claim 1, wherein the DNA in the sample is highly fragmented.

5. The method of claim 1, wherein the library of DNA molecules of (b)(i) is fragmented human genomic DNA.

6. The method of claim 5, wherein the fragmented human genomic DNA is enriched for non-repetitive sequences.

7. The method of claim 1, wherein the extracted DNA comprises at least 10 times more environmental DNA than endogenous DNA.

8. The method of claim 1, further comprising sequencing the captured DNA molecules after step (f).

9. The method of claim 1, wherein the hybridizing step (b) is done by PERT or osPERT.

10. The method of claim 1, wherein the RNA promoter is a T7 promoter.

11. The method of claim 1, wherein the substrate comprises magnetic beads.

12. The method of claim 1, wherein the universal adaptor is 15 to 100 bases in length and is ligated to both ends of the DNA molecules in the extracted DNA.

13. The method of claim 1, wherein the affinity-tag is a biotin moiety and the capture agent is streptavidin or avidin.

14. The method of claim 1, wherein the RNA oligonucleotide is complementary to at least 50% of the sequence of the universal adaptor.

15. The method of claim 1, wherein the sample comprises nucleic acids from 3 or more sources.

16. The method of claim 1, wherein the sample comprises nucleic acids from 10 or more sources.

17. The method of claim 1, wherein the sample comprises nucleic acids from 100 or more sources.

18. The method of claim 1, wherein the sample comprises nucleic acids from 1000 or more sources.

19. The method of claim 1, wherein the sample comprises nucleic acids from 10000 or more sources.

20. The method of claim 1, wherein the sample comprises DNA from multiple individuals.

21. The method of claim 20, wherein the method comprises ligating a molecular barcode to the extracted DNA.

22. The method of claim 21, wherein the universal adaptor comprises the molecular barcode.

23. The method of claim 1, wherein the RNA oligonucleotides are complementary to the entire contiguous sequence of the universal adaptor.

* * * * *

SEQUENCE LISTING

<160> NUMBER OF SEQ ID NOS: 7

<210> SEQ ID NO 1
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 1
gatcttaagg ctagagtact aatacgactc actataggg                              39

<210> SEQ ID NO 2
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 2
ccctatagtg agtcgtatta gtactctagc cttaagatc                              39

<210> SEQ ID NO 3
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 3
agtactaata cgactcacta tagg                                              24

<210> SEQ ID NO 4
<211> LENGTH: 82
<212> TYPE: DNA
<213> ORGANISM: Artificial Sequence
<220> FEATURE:
<223> OTHER INFORMATION: Synthetic oligonucleotide

<400> SEQUENCE: 4

```
agatcggaag agcgtcgtgt agggaaagag tgtagatctc ggtggtcgcc gtatcattcc    60
tatagtgagt cgtattagta ct                                            82

<210> SEQ ID NO 5
<211> LENGTH: 88
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 35, 36, 37, 38, 39, 40
<223> OTHER INFORMATION: n = A,T,C or G

<400> SEQUENCE: 5
agatcggaag agcacacgtc tgaactccag tcacnnnnnn atctcgtatg ccgtcttctg    60
cttgcctata gtgagtcgta ttagtact                                      88

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 6
aatgatacgg cgaccaccga                                               20

<210> SEQ ID NO 7
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 7
caagcagaag acggcatacg a                                             21
```